United States Patent [19]

Nickl et al.

[11] 3,993,683
[45] Nov. 23, 1976

[54] BIPHENYLYL DERIVATIVES

[75] Inventors: Josef Nickl; Erich Müller, both of Biberach, Riss; Berthöld Narr, Mettenberg; Walter Haarmann, Biberach, Riss; Wolfgang Schröter, Biberach, Riss; Rüdolf Kadatz, Biberach, Riss, all of Germany

[73] Assignee: Boehringer Ingelheim GmbH, Ingelheim am Rhine, Germany

[22] Filed: May 14, 1975

[21] Appl. No.: 577,169

[30] Foreign Application Priority Data

| | | |
|---|---|---|
| May 20, 1974 | Germany | 2424475 |
| Jan. 11, 1975 | Germany | 2500944 |
| Jan. 30, 1975 | Germany | 2503770 |
| Feb. 26, 1975 | Germany | 2508243 |
| Feb. 26, 1975 | Germany | 2508244 |

[52] U.S. Cl. ............ 260/470; 260/243 B; 260/247.1 R; 260/290 R; 260/293.73; 260/465 R; 260/465 G; 260/515 M; 260/520 R; 260/515 A; 260/558 S; 260/559 T; 260/607 R; 260/607 A; 424/263; 424/267; 424/246; 424/248; 424/308; 424/317; 424/324; 424/337

[51] Int. Cl.$^2$ ............................ C07C 149/40

[58] Field of Search .................... 260/470

[56] References Cited
OTHER PUBLICATIONS
Janczewski et al., Chem. Abs. 68 1968.

*Primary Examiner*—Howard T. Mars
*Attorney, Agent, or Firm*—Hammond & Littell

[57] ABSTRACT

Compounds of the formula

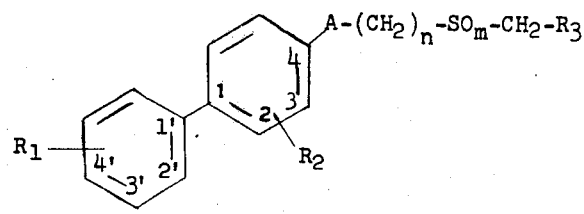

wherein
$R_1$ is hydrogen, fluorine, bromine, methyl, methoxy, methylthio, nitro, cyano or, when A is other than methylene, $R_2$ is hydrogen, $R_3$ is carboxyl, m is 2 and n is 0, also chlorine;
$R_2$ is hydrogen or fluorine;
$R_3$ is hydrogen, methyl, hydroxymethyl, carboxyl, (alkoxy of 1 to 6 carbon atoms)-carbonyl, methoxy-(alkoxy of 1 to 6 carbon atoms)-carbonyl, (alkenyloxy of 2 to 6 carbon atoms)-carbonyl, (aralkoxy of 7 to 12 carbon atoms)-carbonyl, phenoxy-carbonyl, pyridylmethoxy-carbonyl, amino-carbonyl, (alkyl of 1 to 3 carbon atoms-amino)-carbonyl, (dialkyl of 1 to 3 carbon atoms-amino)-carbonyl, phenylamino-carbonyl, morpholino-carbonyl, piperidino-carbonyl, thiomorpholino-carbonyl, (1-oxidothiomorpholino)-carbonyl or (1,1-dioxido-thiomorpholino)-carbonyl;
A is methylene, (alkyl of 1 to 3 carbon atoms)-methylene, di-(alkyl of 1 to 3 carbon atoms)-methylene, hydroxymethyl-methylene, hydroxymethylene or carbonyl;
*m* is 1 or 2; and
*n* is 0, 1, 2 or 3;
and, when $R_3$ is carboxyl, non-toxic salts thereof formed with an inorganic or organic base. The compounds as well as the salts are useful as antithrombotics, anticholesteremics and anticoagulants.

2 Claims, No Drawings

BIPHENYLYL DERIVATIVES

This invention relates to novel derivatives of biphenyl and salts thereof, as well as to various methods of preparing these compounds.

More particularly, the present invention relates to a novel class of biphenyl derivatives represented by the formula

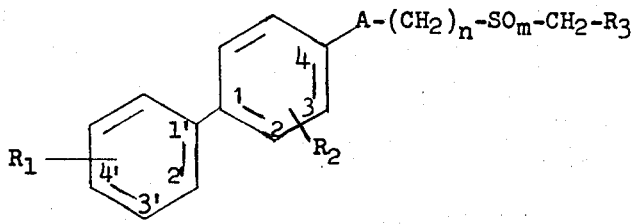

(I)

wherein
R_1 is hydrogen, fluorine, bromine, methyl, methoxy, methylthio, nitro, cyano or, when A is other than methylene, $R_2$ is hydrogen, $R_3$ is carboxyl, $m$ is 2 and n is 0, also chlorine;
$R_2$ is hydrogen or fluorine;
$R_3$ is hydrogen, methyl, hydroxymethyl, carboxyl, (alkoxy of 1 to 6 carbon atoms)-carbonyl, methoxy-(alkoxy of 1 to 6 carbon atoms)-carbonyl, (alkenyloxy of 2 to 6 carbon atoms)-carbonyl, (aralkoxy of 7 to 12 carbon atoms)-carbonyl, phenoxy-carbonyl, pyridylmethoxy-carbonyl, amino-carbonyl, (alkyl of 1 to 3 carbon atoms-amino)-carbonyl, (dialkyl of 1 to 3 carbon atoms-amino)-carbonyl, phenylamino-carbonyl, morpholino-carbonyl, piperidino-carbonyl, thiomorpholino-carbonyl, (1-oxidothiomorpholino)-carbonyl or (1,1-dioxido-thiomorpholino)-carbonyl;
A is methylene, (alkyl of 1 to 3 carbon atoms)-methylene, di-(alkyl of 1 to 3 carbon atoms)-methylene, hydroxymethyl-methylene, hydroxy-methylene or carbonyl;
$m$ is 1 or 2; and
$n$ is 0, 1, 2 or 3;
diastereoisomers thereof, optically active antipodes thereof, and, when $R_3$ is carboxyl, non-toxic salts thereof formed with an inorganic or organic base.

Especially preferred embodiments of $R_3$ are methoxycarbonyl, ethoxycarbonyl, (2-methoxy-ethoxy)-carbonyl, n-propoxy-carbonyl, isopropoxy-carbonyl, n-butoxy-carbonyl, isobutoxy-carbonyl, n-pentyloxy-carbonyl, isoamyloxy-carbonyl, hexyloxy-carbonyl, benzyloxy-carbonyl, allyloxy-carbonyl, crotyloxy-carbonyl, amino-carbonyl, methylamino-carbonyl, dimethylamino-carbonyl, isopropylamino-carbonyl and phenylamino-carbonyl.

The compounds embraced by formula I above may be prepared by the following methods:

Method A

For the preparation of a compound of the formula I, wherein $R_3$ is other than thiomorpholino-carbonyl, and $R_1$ is other than methylthio when m is 2, by oxidation of a thioether of the formula

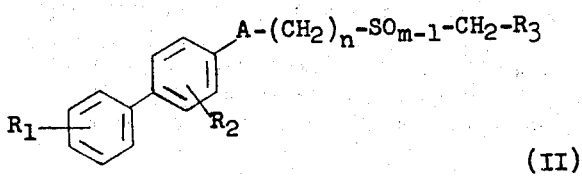

(II)

wherein $R_1$, $R_2$, $R_3$, A, m and n have the meanings defined above.

The oxidation is preferably carried out in the presence of a solvent, such as in water, water/pyridine, acetone, glacial acetic acid, dilute sulfuric acid or trifluoroacetic acid, depending on the particular oxidizing agent which is used, and advantageously at temperatures between −80° and 100° C.

For the preparation of a compound of the formula I wherein $m$ is 1, the oxidation is advantageously effected with an equimolar quantity of a suitable oxidizing agent, such as with hydrogen peroxide in glacial acetic acid at 0° to 20° C, or in acetone at 0° to 60° C; with a peracid, such as performic acid in glacial acetic acid or trifluoroacetic acid at 0° to 50° C; with sodium metaperiodate in aqueous methanol or ethanol at 15 to 25° C; with tert.butyl hypochlorite in methanol at −80 to −30° C; with iodobenzene dichloride in aqueous pyridine at 0° to 5° C; with nitric acid in glacial acetic acid at 0° to 20° C; with chromic acid in glacial acetic acid or in acetone at 0° to 20° C; and with sulfuryl chloride in methylene chloride at −70° C. The thioether-chloro-complex thus obtained is then hydrolyzed with aqueous ethanol.

For the preparation of a compound of the formula I, wherein $m$ is 2, the oxidation is effected with one or with two mol equivalents of a suitable oxidizing agent, such as with hydrogen peroxide in glacial acetic acid at 20° to 100° C or in acetone at 0 to 60° C; with a peracid, such as performic acid or m-chloroperbenzoic acid, in glacial acetic acid, trifluoroacetic acid or chloroform at temperatures between 0° and 50° C; with nitric acid in glacial acetic acid at 0° to 20° C; with chromic acid or potassium permanganate in glacial acetic acid, water/sulfuric acid or acetone at 0° to 20° C. Thus, if in a compound of the formula II m is 1, the reaction is preferably carried out with 2 molar equivalents of the particular oxidizing agent, and if $m$ is 2, analogously with one equivalent.

Method B

For the preparation of a compound of the formula I, wherein $R_3$ is other than hydrogen, methyl, hydroxymethyl or carboxyl, by reacting a compound of the formula

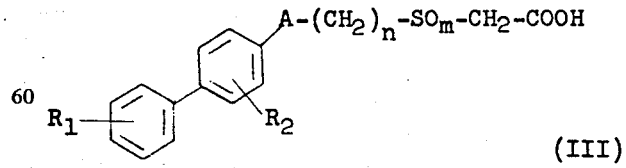

(III)

wherein $R_1$, $R_2$, A, n and m have the meanings previously defined, or a halide or anhydride thereof, with a compound of the formula $R_3' - X$  (IV)

wherein $R_3'$ has the same meaning as $R_3$ except hydrogen, methyl, hydroxymethyl or carboxyl, and X is hydroxyl, chlorine, bromine, iodine, sulfonyl or phosphoryl, diazo, or also hydrogen if $R_3'$ is amino.

The reaction is carried out in the presence of a solvent, such as ether, chloroform, benzene, tetrahydrofuran, dioxane, dimethyl sulfoxide, dimethylformamide, hexamethylphosphoric acid-triamide, or in the presence of an excess of the compound of the formula IV, and optionally in the presence of an acid-activating and/or dehydrating agent and optionally in the presence of a base, at temperatures between $-20°$ and $150°$ C.

If compound IV is a carbinol, such as methanol, ethanol, propanol, isoamylalcohol, n-hexanol, 2-methoxyethanol, allyl alcohol, phenol or benzyl alcohol, the reaction is carried out in the presence of an acid, such as sulfuric acid, p-toluene-sulfonic acid or hydrogen chloride; or an acid-activating agent such as phosphorus oxychloride, thionyl chloride or chlorosulfonic acid; or a dehydrating agent, such as cyclohexylcarbodiimide, carbonyldiimidazole or 2,2-dimethoxypropane; or with a corresponding chloroformate, optionally in the presence of a base, such as potassium carbonate or triethylamine; and preferably at temperatures between 20 and 100° C.

If compound IV is a sulfate, such as dimethyl sulfate; or a phosphate, such as triethylphosphate; or a halide, such as methyl iodide, ethyl iodide or allyl bromide, the reaction is carried out in a dipolar aprotic solvent in the presence of a base, such as potassium carbonate, calcium hydroxide or sodium hydroxide, and preferably at temperatures between 20° and 80° C. The reaction may, however, also be carried out under the conditions of a phase transfer-catalyzed 2-phase reaction, for example between chloroform and water, in the presence of a quaternary ammonium salt, such as tetrabutyl ammonium iodide.

If compound IV is an amine, such as ammonia, methylamine, dimethyl amine, morpholine, piperidine, thiomorpholine or 1-oxidothiomorpholine, the reaction is carried out in the presence of a dehydrating agent, such as cyclohexylcarbodiimide or carbonyl diimidazole, preferably in the presence of a solvent, such as dioxane or tetrahydrofuran, and at temperatures between 10° and 50° C.

Method C

For the preparation of compound of the formula I, wherein A is hydroxymethylene, $R_3$ is hydrogen, and n and m are 1, by reacting an aldehyde of the formula

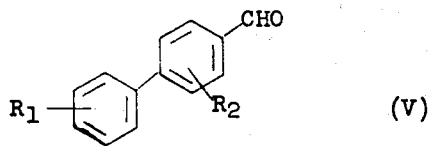

wherein $R_1$ and $R_2$ have the meanings previously defined, with dimethyl sulfoxide in the presence of a base.

The reaction is preferably carried out in the presence of an aprotic solvent, such as dimethyl sulfoxide, in the presence of a base, such as potassium tert.butylate or sodium hydride, and at temperatures between 50° and 150° C.

Method D

For the preparation of a compound of the formula I, wherein A is hydroxymethylene, by reducing a compound of the formula

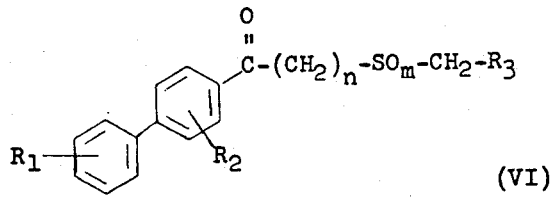

wherein $R_1$, $R_2$, $R_3$, n and m have the meanings previously defined.

The reduction is preferably carried out with a complex metal hydride, such as sodium borohydride, in the presence of a solvent, such as water, methanol or water/methanol, and at temperatures between 0° and 25° C.

The end products obtained pursuant to methods A to D may, if desired, be separated into their optically active antipodes by conventional methods, such as by chromatography on an optically active carrier or by fractional crystallization of their salts formed with optically active bases.

If the end product obtained by any of the above described methods is one of the formula I wherein $R_3$ is a carboxylic ester group, the same may, if desired, by converted into the corresponding free caboxylic acid by hydrolysis.

Those compounds of the formula I wherein $R_3$ is free carboxyl may, if desired, be converted into non-toxic, pharmacologically acceptable salts thereof formed with inorganic or organic bases. Examples of such salts are those formed with sodium hydroxide, potassium hydroxide, cyclohexylamine or the like.

The starting compounds of the formulas II to VI may be prepared by methods described in the literature, as illustrated in Examples A to N below.

The following examples illustrate the present invention and will enable others skilled in the art to understand it more completely. It should be understood, however, that the invention is not limited solely to the particular examples given below. Preliminary remarks:
1. The following commercially available carriers were used for thin-layer chromatography:
   Carrier 1 = Polygram SIL G/UV$^{254}$, manufactured by Macherey, Nagel & Co.
   Carrier 2 Silicagel Siliagel - prepared plates 60 F – 254, manufactured by E. Merck
2. The following solvents were used: Tetrahydrofuran dried over potassium hydroxide, or dimethyl sulfoxide dried over a molecular sieve (4 AE).
3. For column chromatography, silicagel manufactured by ICN-Woelm, Eschwege, Germany, (grain size: 0.063 – 0.2 mm) was used.

Preparation of starting compounds:

EXAMPLE A

[1-(2'-Fluoro-4-biphenylyl)-ethylthio]-acetic acid 6.35 gm (0.055 mol) of 80% mercaptoacetic acid were admixed in 70 ml of methanol with a solution of 6.2 gm (0.11 mol) of potassium hydroxide in 6.2 ml of water. To the solution of the dipotassium salt, 11.7 gm (0.05 mol) of 1-(2'-fluoro-4-biphenylyl)-1-chloroethane were added, the reaction mixture was rinsed with 20 ml of methanol and stirred for 18 hours at room temperature. Subsequently, the mixture was evaporated, the residue was digested with acetone, and the precipitated potassium salt was suction-filtered off. The free acid was obtained by dissolving the salt in water and acidifying the solution. M.p. 128°–130° C (from toluene). Yield: 55% of theory.

EXAMPLE B

[1-(2'-Fluoro-4-biphenylyl)-propylthio]-acetic acid methyl ester 101.5 gm (0.905 mol) of potassium tert.butylate, suspended in 500 ml of dimethylformamide, were admixed, while stirring and cooling under exclusion of air, with 96.0 gm (0.905 mol) of thioglycolic acid methyl ester. To the solution of the potassium salt, the mixture was admixed with 205.9 gm (0.822 mol) of 1-chloro-1-(2'-fluoro-4-biphenylyl)-propane [prepared by reduction of 2'-fluoro-4-biphenylyl-ethylketone with sodium borohydride and subsequent reaction of the obtained 1-hydroxy-1-(2'-fluoro-4-biphenylyl)-propane with hydrochloric acid in benzene], and the mixture was stirred for 4 hours at room temperature. Subsequently, 2 liters of water were added, and the reaction product was isolated by extraction with ethyl acetate, and washing, drying and evaporating of the extract. Yield: 254 gm (97% of theory); oil, $R_f$-value: 0.5 (cyclohexane-ethyl acetate = 9:1 on silicagelpolygram-plates).

The following starting compounds were prepared in analogous manner:
(4-Biphenylyl-methylthio)-acetic acid methyl ester; oil, $R_f$-value: 0.6 (cyclohexane-ethyl acetate = 4:1 on silicagel-polygram-plates)
[2-(4-Biphenylyl)-ethylthio]-acetic acid methyl ester; oil, $R_f$-value: 0.5 (cyclohexane-ethyl acetate = 4:1 on silicagel-polygram-plates)
[1-(4-Biphenylyl)-ethylthio]-acetic acid methyl ester; oil, $R_f$-value: 0.6 (cyclohexane-ethyl acetate = 4:1 on silicagel-polygram-plates)
[1-(2'-Fluoro-4-biphenylyl)-ethylthio]-acetic acid methyl ester; oil, $R_f$-value: 0.6 (cyclohexane-ethyl acetate = 4:1 on silicagel-polygram-plates)
[2-(2'-Fluoro-4-biphenylyl)-propylthio]-acetic acid methyl ester; oil, $R_f$-value: 0.6 (cyclohexane-ethyl acetate = 4:1 on silicagel-polygram-plates)
[4-(4-Biphenylyl)-butylthio]-acetic acid methyl ester; oil, $R_f$-value: 0.5 (cyclohexane-ethyl acetate = 4:1 on silicagel-polygram-plates)
[4-(2'-Fluoro-4-biphenylyl)-butylthio]-acetic acid methyl ester; oil, $R_f$-value: 0.7 (cyclohexane-ethyl acetate = 4:1 on silicagel-polygram-plates)
[3-(4-Biphenylyl)-butylthio]-acetic acid methyl ester; oil, $R_f$-value: 0.5 (cyclohexane-ethyl acetate = 4:1 on silicagel-polygram-plates)
[3-(2'-Fluoro-4-biphenylyl)-butylthio]-acetic acid methyl ester; oil, $R_f$-value: 0.5 (cyclohexane-ethyl acetate = 4:1 -on silicagel-polygram-plates)
[1-(2'-Fluoro-4-biphenylyl)-ethylthio]-methyl ether; oil, $R_f$-value: 0.4 (cyclohexane-toluene = 9:1 on silicagelpolygram-plates).

Analysis: $C_{15}H_{15}FS$; mol.wt. 246.36 Calculates: C - 73.13%; H - 6.14%; S - 13.02% Found: C - 73.20%; H - 6.15%; S - 12.90%

EXAMPLE C

[1-(2'-Fluoro-4-biphenylyl)-propylthio]-acetic acid
220 gm of the methyl ester obtained in Example B were hydrolized with 58.2 gm of potassium hydroxide in 900 ml of ethanol by boiling for 1 hour. Subsequently, the mixture was diluted with 1800 ml of water, the neutral components were extracted with ether, and the free acid was precipitated from the alkaline phase. By extraction with ether, and washing, drying and evaporating the ethereal extract, the reaction product was isolated. Yield: 130 gm (62% of theory); oil, $R_f$-value: 0.7 (cyclohexane-ethyl acetate = 1:1 on silicagel-polygram-plates).

The following compounds were prepared in analogous manner:
[1-(2'-Fluoro-4-biphenylyl)-ethylthio]-acetic acid; m.p. 125°–127° C (from benzene-cyclohexane = 2:1)
[2-(2'-Fluoro-4-biphenylyl)-propylthio]-acetic acid; oil, $R_f$-value: 0.35 (benzene/ethyl acetate/methanol = 8:4:2 on pre-prepared silicagel plates).

EXAMPLE D

[1-(2'-Fluoro-4-biphenylyl)-ethylthio]-acetic acid
50 gm (0.23 mol) of 1-(2'-fluoro-4-biphenylyl)-1-hydroxy-ethane, m.p. 88° C, (prepared from 2'-fluoro-4-biphenylyl-methyl-ketone by reduction with sodium borohydride in methanol) were dissolved in 500 ml of benzene, 32.2 gm (0.276 mol) of 80% mercapto-acetic acid and 1 gm of p-toluene-sulfonic acid were added, and the mixture was heated at its boiling point for 1 hour, using an apparatus equipped with a water trap. 20.5 ml of water were separated. The benzene solution was washed with water after cooling, dried and evaporated. The crystalline residue was recrystallized from benzene/cyclohexane (2:1), whereby 38.0 gm (61.5% of theory) of the title compound, m.p. 125°–127° C, were obtained.

The following compounds were prepared in analogous manner:
[α,α-Dimethyl-(2'-fluoro-4-biphenylyl)-methylthio]-acetic acid, m.p. 100°–101° C (cyclohexane), and by subsequent esterification
[α,α-Dimethyl-(2'-fluoro-4-biphenylyl)-methylthio]-acetic acid-methyl ester; oil, $R_f$-value: 0.4 (cyclohexane-ethyl acetate = 9:1 on silicagel-polygram-plates).

EXAMPLE E

[1-(2'-Chloro-4-biphenylyl)-ethylthio]-acetic acid
[1-(2'-Chloro-4-biphenylyl)-ethylthio]-acetic acid methyl ester 294 gm (1.17 mol) of 1-(2'-chloro-4-biphenylyl)-1-chloro-ethane and 149.2 gm (1.4 mol) of thioglycolic acid methyl ester were dissolved in 1 liter of dimethyl sulfoxide, and 194.3 gm (1.4 mol) of potassium carbonate were added to the solution in small portions, while stirring vigorously and cooling on ice water. After stirring the mixture for 4 hours, 3 liters of water were added. The reaction product was extracted with toluene, and after washing the extract with water and drying it over magnesium sulfate, the solvent was removed in vacuo. Yield: 359.0 gm (95.5% of theory). $R_f$-value: 0.6 on carrier 1 with cyclohexane/ethyl acetate = 4:1.

2. [1-(2'-Chloro-4-biphenylyl)-ethylthio]-acetic acid
359 gm of the methyl ester thus obtained were boiled with 94.2 gm (1.68 mol) of potassium hydroxide in 1200 ml of ethanol for 1 hour. Subsequently, the mixture was evaporated in vacuo, the crystalline residue was taken up in water, and the aqueous mixture was extracted with ether to remove neutral components. By acidification, the free acid was obtained as a slowly crystallizing oil. Yield: 215.0 gm (62.5% of theory); m.p. 114°–119° C (from toluene).

The following compound was prepared in analogous manner:
[1-(2-Fluoro-4-biphenylyl)ethylthio]-acetic acid, m.p. 146–149° C (from toluene).

EXAMPLE F

[1-(2'-Chloro-4-biphenylyl)-ethylthio]-acetic acid amide 63.0 gm (0.205 mol) of [1-(2'-chloro-4-biphenylyl)-ethylthio]-acetic acid were dissolved in 630 ml of dry tetrahydrofuran, and 33.3 gm (0.246 mol) of carbonyldiimidazole were added. After stirring the mixture for ½ hour, dry ammonia was introduced into 300 ml of the obtained solution of the imidazolide (corresponding to 0.0683 mol), while cooling slightly, until the mixture was saturated. Subsequently, the mixture was stirred for 2.5 hours more and then evaporated in vacuo. The residue was distributed between water and ethyl acetate, and washed several times with dilute hydrochloric acid. The organic layer was dried and evaporated. Yield: 100% of theory; oil, $R_f$-value: 0.2 on carrier 1 with cyclohexane/ethyl acetate = 1:1.

The following compounds were prepared in analogous manner:
[1-(2'-Chloro-4-biphenylyl)-ethylthio]-acetic acid piperidide; oil, $R_f$-value: 0.6 on carrier 1 with cyclohexane/ethyl acetate = 1:1
[1-(2'-Chloro-4-biphenylyl)-ethylthio]-acetic acid morpholide, oil, $R_f$-value: 0.4 on carrier 1 with cyclohexane/ethyl acetate = 1:1.

EXAMPLE G

[1-(2'-Fluoro-4-biphenylyl)-ethylthio]-acetic acid amide a. 199.8 gm (0.69 mol) of [1-(2'-fluoro-4-biphenylyl)-ethylthio]-acetic acid (m.p. 127°–129° C) were admixed with 250 ml of thionyl chloride, and the mixture was boiled for 1 hour, whereby the acid dissolved. The acid chloride was obtained as an oil after distilling off the excess thionyl chloride in vacuo.

b. 30.9 gm of the acid chloride thus obtained were dissolved in 50 ml of acetone, and the solution was poured into 38.5 ml of concentrated ammonia, while cooling on ice and stirring. Afterwards, the mixture was stirred for 30 minutes more, evaporated, and the residue was distributed between dilute hydrochloric acid and ether. The ether solution was washed, dried and evaporated, and the oily residue (25.4 gm) was purified by chromatography on 2000 gm of silicagel with cyclohexane/ethyl acetate = 1:1. The fractions with an $R_f$-value of 0.2 (on carrier 1) were combined, evaporated and recrystallized from cyclohexane/toluene = 2:1. Yield: 8.7 gm (30.1% of theory); m.p. 77°–79° C.

The following compounds were prepared in analogous manner:
[1-(2'-Fluoro-4-biphenylyl)-ethylthio-acetic acid methyl amide, m.p. 94-96° C (from cyclohexane/toluene = 2:1).
[1-(2'-Fluoro-4-biphenylyl)-ethylthio]-acetic acid dimethyl amide; oil, $R_f$-value: 0.3 on carrier 1 with cyclohexane/ethyl acetate = 1:1.
[1-(2'-Fluoro-4-biphenylyl)ethylthio]-acetic acid piperidide; oil, $R_f$-value: 0.5 on carrier 1 with cyclohexane/ethyl acetate = 1:1.
[1-(2'-Fluoro-4-biphenylyl)-ethylthio]-acetic acid morpholide; oil, $R_f$-value: 0.4 on carrier 1 with cyclohexane/ethyl acetate = 1:1.
[1-(2'-Fluoro-4-biphenylyl)-ethylthio]-acetic acid thiomorpholide; oil, $R_f$-value: 0.45 on carrier 1 with cyclohexane/ethyl acetate = 1:1.

EXAMPLE H

Ethyl [2-(2'-fluoro- 4-biphenylyl)-2-oxoethyl]-sulfide 20 gm (68.2 millimols) of bromomethyl-(2'-fluoro-4-biphenylyl)-ketone (m.p.: 73°–75° C) and a solution of 4.66 gm (75 millimols) of ethanethiol in 120 ml of chloroform were admixed, while cooling to 0°–5° C, with 7.6 gm (75 millimols) of triethylamine and the mixture was stirred at room temperatue for 1 hour. The mixture was then washed with water, dried and evaporated, and the residue was recrystallized from ethanol. Yield: 87% of theory m.p. 64°–67° C.

The following compounds were prepared in analogous manner:
2-Hydroxyethyl-[2-(4-biphenylyl)-2-oxo-ethyl]sulfide, m.p. 67°–69° C (from isopropanol);
2-Hydroxyethyl-[2-(2'-fluoro-4-biphenylyl)-2-oxoethyl-sulfide, m.p. 48°–50° C (from benzene/cyclohexane = 1:1);
[2-(4-Biphenylyl)-2-oxo-ethylthio]acetic acid methyl ester, m.p. 86°–87° C (from methanol);
[2-(4-Biphenylyl)-2-oxo-ethylthio]acetic acid ethyl ester, m.p. 60° C (from n-butanol);
[2-(2'-Fluoro-4-biphenylyl)-2-oxo-ethylthio]acetic acid methyl ester, m.p. 80°–82° C (from n-propanol).

EXAMPLE I

[2-(2'-Fluoro-4-biphenylyl)-2-oxo-ethylthio]acetic acid

A solution of 0.1 mol of thioglycolic acid and 0.1 mol of sodium hydroxide in 20 ml of water was added, while vigorously stirring to a solution of 0.1 mol of bromomethyl(2'-fluoro-4-biphenylyl)-ketone in 150 ml of acetone. After the exothermic reaction was finished, the mixture was diluted with water and acidified, and the precipitated reaction product was recrystallized from ethyl acetate after drying. Yield: 86% of theory; m.p. 149°–151° C.
[2-(4'-Fluoro-4-biphenylyl)-2-oxo-ethylthio]acetic acid, m.p. 142°–144° C (from benzene), was prepared in analogous manner.

EXAMPLE J

2-Hydroxyethyl-[2-(4-biphenylyl)-2-hydroxy-ethyl]-sulfide 8.0 gm of 2-hydroxyethyl-[2-(4-biphenylyl)-2-oxoethyl]sulfide were reduced in 100 ml of methanol with 560 mgm of sodium borohydride in 5 ml of water a room temperature. The reaction product was precipitated with water and isolated as a slowly crystallizing oil by extraction with ethyl acetate. Yield: 8 gm (100% of theory); $R_f$-value: 0.4 on silicagel-polygram-plates with benzene/ethyl acetate = 1:1 as the eluant.
2-Hydroxyethyl-[2-(2'-fluoro-4-biphenylyl)-2-hydroxyethyl]-sulfide, an oil, $R_f$-value: 0.3 on silicagel-polygram-plates with benzene/ethyl acetate = 1:1 as the eluant, was prepared in analogous manner.

EXAMPLE K

[2-(4-Biphenylyl)-2-oxo-ethylthio]acetic acid isopropylamide 6 gm of [2-(4-biphenylyl)-2-oxo-ethylthio]acetic acid chloride (prepared from the corresponding acid with thionyl chloride) were admixed with 2.6 gm of isopropylamine in 50 ml of dioxane. After standing overnight, the reacton product was precipitated with water, suction-filtered off, dried and recrystallized from benzene/cyclohexane = 1:1. M.p. 120°–121° C.

The following compounds were prepared in analogous manner:

[2-(4-Biphenylyl)-2-oxo-ethylthio]acetic acid amide, m.p. 172°–174° C (from n-butanol);

[2-(4-Biphenylyl)-2-oxo-ethylthio]acetic acid thiomorpholide, m.p. 116°–118° C (from benzene/cyclohexane = 1:1);

[2-(4-Biphenylyl)-2-oxo-ethylthio]acetic acid anilide, m.p. 123°–125° C (from benzene/cyclohexane = 1:1);

[2-(2'-Fluoro-4-biphenylyl)-2-oxo-ethylthio]acetic acid isopropylamide, m.p. 91°–93° C (from benzene/cyclohexane = 1:1);

[2-(2'-Fluoro-4-biphenylyl)-2-oxo-ethylthio]acetic acid thiomorpholide, m.p. 122°–124° C (from cyclohexane/benzene = 1:1).

EXAMPLE L

[1-(4'-Methoxy-4-biphenylyl)-ethylthio]acetic acid methyl ester (4'-Methoxy-4-biphenyl)-methyl-ketone [see W. S. Johnson et al, J. Amer. Chem. Soc. 68, 1648 (1946)] was reduced with sodium borohydride to 1-(4'-methoxy-4-biphenylyl)-ethanol (m.p. 120°–122° C, from cyclohexane), and the carbinol was converted into 1-(4'-methoxy-4-biphenylyl)-1-chloroethane, m.p. 122°–124° C (from cyclohexane), with hydrogen chloride. 5.2 gm of 1-(4'-methoxy-4-biphenylyl)-1-chloroethane (0.021 mol) were admixed in 21 ml of dry dimethyl sulfoxide with 2.7 gm (0.026 mol) of thioglycolic acid methyl ester and then with 3.5 gm (0.026 mol) of dry potassium carbonate. The mixture was stirred at room temperature for 45 minutes. The reaction product was precipitated with water, suction-filtered off, washed and dried. Yield: 6.8 gm (100% of theory); m.p. 59°–61° C. A sample recrystallized from cyclohexane, analized as follows:

$C_{18}H_{20}O_3S$; mol.wt. 316.43 Calculated: C - 68.33%; H - 6.37%; S - 10.13% Found: C - 68.00%; H - 6.52%; S - 10.27%

The following compounds were prepared in analogous manner:

(2'-Fluoro-4-biphenylyl)-methyl-thioacetic acid methyl ester, oil, $R_f$-value: 0.5 on carrier 1 with cyclohexane/ethyl acetate = 4:1; yield: 80% of theory. Therefrom by hydrolysis:

(2'-Fluoro-4-biphenylyl)-methyl-thioacetic acid, m.p. 94° C, sintering at 75°–78° C

[1-(4'-Fluoro-4-biphenylyl)-ethylthio]acetic acid methyl ester, oil, $R_f$-value: 0.6 on carrier 1 with petroleum ether/ethyl acetate = 3:1, yield: 99% of theory.

[1-(4'-Chloro-4-biphenylyl)-ethylthio]acetic acid methyl ester, oil, $R_f$-value: 0.5 on carrier 1 with cyclohexane/ethyl acetate = 4:1, yield: 95% of theory. Therefrom by hydrolysis:

[1-(4'-Chloro-4-biphenylyl)-ethylthio]acetic acid, m.p. 130° C (from toluene); yield: 78% of theory.

[1-(4'-Bromo-4-biphenylyl)-ethylthio]acetic acid methyl ester, yield: 79% of theory; m.p. 46°–49° C (from isopropanol).

[1-(4'-Methyl-4-biphenylyl)-ethylthio]acetic acid methyl ester, oil, $R_f$-value: 0.8 on carrier 1 with petroleum ether/ethyl acetate = 7:3. Therefrom by hydrolysis:

[1-(4'-Methyl-4-biphenylyl)-ethylthio]acetic acid, crystalline material of $R_f$-value 0.4 on carrier 1 with petroleum ether/ethyl acetate = 7:3, yield: 41% of theory.

[1-(4'-Methylmercapto-4-biphenylyl)-ethylthio]acetic acid methyl ester, yield: 83.4% of theory; m.p. 74°–76° C (from ethanol).

[1-(2'-Nitro-4-biphenylyl)-ethylthio]acetic acid methyl ester, oil, $R_f$-value: 0.45 on carrier 1 with cyclohexane/ethyl acetate = 4:1; yield: 87% of theory.

[1-(3'-Chloro-4-biphenylyl)-ethylthio]acetic acid methyl ester, oil, $R_f$-value: 0.55 on carrier 1 with cyclohexane/ethyl acetate = 4:1; yield: 93% of theory.

[1-(2',4'-Dichloro-4-biphenylyl)-ethylthio]acetic acid methyl ester, oil, $R_f$-value: 0.4 on carrier 1 with petroleum ether/ethyl acetate = 7:3; yield: 76% of theory.

[1-(2,2'-Difluoro-4-biphenylyl)-ethylthio]acetic acid methyl ester, oil, $R_f$-value: 0.5 on carrier 1 with cyclohexane/ethyl acetate = 4:1; yield: 94% of theory.

[1-(2-Fluoro-4'-bromo-4-biphenylyl)-ethylthio]acetic acid methyl ester, oil, $R_f$-value: 0.6 on carrier 1 with cyclohexane/ethyl acetate = 4:1; yield: 95% of theory.

EXAMPLE M

[1-(2'-Cyano-4-biphenylyl)-ethylthio]acetic acid methyl ester a. [1-(2'-Amino-4-biphenylyl)-ethylthio]acetic acid methyl ester.

22.0 gm (0.066 mol) of [1-(2'-nitro-4-biphenylyl)-ethylthio]-acetic acid methyl ester were hydrogenated in 220 ml of ethanol in the presence of 10 gm of Raney nickel at room temperature and at a hydrogen pressure of 5 atmospheres. After the absorption of hydrogen had ceased, the catalyst was suction-filtered off, and the filtrate was evaporated. The residue was an oil, $R_f$-value: 0.3 on carrier 1 with cyclohexane/ethyl acetate = 4:1; yield: 18.2 gm (91% of theory).

b. [1-(2'-Cyano-4-biphenylyl)-ethylthio]acetic acid methyl ester 18.2 gm (0.0605 mol) of the methyl ester were admixed with 15.3 ml of hydrochloric acid and 30 ml of water in 20 ml of tetrahydrofuran, and diazotized at 0°–5° C with 4.4 gm (0.0635 mol) of sodium nitrite in 10 ml of water. The diazonium salt solution was added to a warm solution of 60° C of $K_2[Cu(CN)_3]$ (prepared from 18 gm of $CuSO_4 . 5H_2O$, 5.1 gm $NaHSO_3$ and 5.1 gm KCN, and dissolving of the CuCN-precipitate in a solution of 9.4 gm of KCN in 25 ml. of water). The reaction product precipitated as a brown oil, accompanied by nitrogen evolution. The product was refluxed for a short time, cooled and extracted with ethyl acetate. The evaporation residue of the extract (15.2 gm) was purified by chromatography on 900 gm of silicagel with cyclohexane/ethyl acetate = 4:1. The fractions with an $R_f$-value of 0.45 on carrier 2 with cyclohexane/ethyl acetate = 4:1 were combined and evaporated. Yield: 7.0 gm of an oil (37% of theory) IR-spectrum (in methylene chloride): CN at 2210 $cm^{-1}$, ester-CO at 1730 $cm^{-1}$, UV-spectrum (in ethanol): maxima at 260 and 290 nm (log$\epsilon$ = 4.1 and 3.8, respectively).

EXAMPLE N

[1-(2'-Fluoro-4-biphenylyl)-2-hydroxy-ethylthio]acetic acid methyl ester (2'-Fluoro-4-biphenylyl)-bromomethyl-ketone, m.p. 73°–75° C, [prepared by bromination of (2'-fluoro-4-biphenylyl)-methylketone was converted into (2'-fluoro-4-biphenylyl)acetoxy-methyl-ketone (m.p.

94°–96° C) in dimethylformamide with potassium acetate. By reduction with sodium borohydride in methanol-water (2'-fluoro-4-biphenylyl)-ethane-diol (m.p. 135°–137° C, from ethanol) was formed. By further reaction with anhydrous hydrogen chloride in toluene, 1-(2'-fluoro-4-biphenylyl)-1-chloro-2-hydroxyethane was obtained, which was purified by column chromatography on silicagel. Oil, $R_f$-value: 0.2 on carrier 2 with cyclohexane/ethyl acetate = 4:1.

20 gm of the product thus obtained were reacted with 8.75 gm of thioglycolic acid methyl ester and 11.5 gm of potassium carbonate in 70 ml of dimethyl sulfoxide. From the obtained reaction product (oil, $R_f$-value: 0.4 on carrier 1 with cyclohexane/ethyl acetate = 2:1) [1-(2'-fluoro-4-biphenylyl)-2-hydroxy-ethylthio]acetic acid, m.p. 115°–117° C (from cyclohexane/ethyl acetate = 1:2, was obtained by hydrolysis. Preparation of end products of the formula I:

EXAMPLE 1

Diastereoisomeric [1-(2'-fluoro-4-biphenylyl)-ethylsulfinyl]-acetic acids a. Difficulty soluble isomer A suspension of 1477 gm (5.1 mol) of [1-(2'-fluoro-4-biphenylyl)ethylthio]-acetic acid in 5.1 liter of glacial acetic acid was admixed over a period of 30 minutes at 15° C with 495 gm (5.35 mol) of 36.8% hydrogen peroxide, while vigorously stirring. Subsequently, the temperature of the mixture was allowed to rise to 20° C. The starting material dissolved almost completely during the reaction, and after some time the reaction product crystallized out. After standing overnight, the product was suction-filtered off, washed with glacial acetic acid and then with petroleum ether, and dried at 40° C. Yield: 994 gm (63% of theory); m.p. 164°–165° C (decomp.).

Analysis: $C_{16}H_{15}FO_3S$; mol.wt. 306.37 Calculated: C - 62.73%; H - 4.94%; S - 10.47% Found: C - 62.90%; H - 5.03%; S - 10.70%

NMR-spectrum (deutero-dimethyl sulfoxide):
$CH_3$: Doublet at 1.7 ppm
CH : Quartet at 4.38 ppm ($J_H$, $CH_3$ = 7Hz)
$CH_2$ : Double doublet at 3.65 ppm; ($\delta\tau$ = about 18 Hz; J=14 Hz)

b. Easily soluble isomer

The acetic acid filtrate obtained in the separation of the difficulty soluble isomer was admixed with 5.1 liters of water. The obtained crystals were suction-filtered off and dried. 80 gm of the obtained 446 gm of the product were recrystallized three times from ethyl acetate. Yield: 29 gm; m.p. 149°–150° C (decomp.).

Analysis: $C_{16}H_{15}FO_3S$; mol. wt. 306.37 Calculated: C - 62.73%; H - 4.94%; S - 10.47% Found: C - 63.00%; H - 5.06%; S - 10.60%

NMR-spectrum (deutero-dimethyl sulfoxide):
$CH_3$ : Doublet at 1.7 ppm
CH : Quartet at 4.25 ppm ($J_H$, $CH_3$ = 7Hz)
$CH_2$ : Double doublet at 3.48 ppm; ($\delta\tau$ = about 36 Hz; J=15 Hz).

EXAMPLE 2

[1-(2'-Fluoro-4-biphenylyl)-ethylsulfinyl]-acetic acid, difficulty soluble isomer:

Separation into the optically active antipodes

A solution of 53.5 gm (0.175 mol) of [1-(2'-fluoro-4-biphenylyl)-ethylsulfinyl]-acetic acid, m.p. 164°–165° C (decomp.), in 400 ml of chloroform/ethanol = 3:1, was admixed with a solution of 51.5 gm (0.175 mol) of cinchonidine ($[\alpha]_D^{20}$ = − 178°) in 400 ml of chloroform/ethanol = 3:1. The clear solution of the salt was evaporated, and the foamy residue was dissolved in 500 ml of hot benzene. Upon standing overnight, the levorotatory acid crystallized out as its cinchonidine salt. This salt was suction-filtered off (72.0 gm, m.p. 140°–144° C) and recrystallized from 4 liters of cyclohexane/ethanol = 8:1. 40.5 gm (77% of theory) of the cinchonidine salt, m.p. 146°–148° C (decomp.) were obtained. By acidification and recrystallization from isopropanol, the free levorotatory acid, m.p. 168°–170° C, $[\alpha]_D^{20}$ = − 131.5° (c = 0.5, methanol), was obtained.

From the benzene filtrate of the cinchonidine-salt-precipitation 12.9 of the free dextrorotatory acid, m.p. 165°–167° C, $[\alpha]_D^{20}$ = + 100° (c = 0.5, methanol), were obtained by acidification and recrystallization from isopropanol.

EXAMPLE 3

[1-(2'-Fluoro-4-biphenylyl)-propylsulfinyl]-acetic acid, was prepared analogously to Example 1 from [1-(2'-fluoro-4-biphenylyl)-propylthio]-acetic acid by oxidation with hydrogen peroxide in glacial acetic acid. Yield: 55.4% of theory; m.p. 136°–137° C (ethyl acetate).

Analysis: $C_{17}H_{17}FO_3S$; mol.wt. 320.39 Calculated: C - 63.73%; H - 5.35%; S - 10.01% Found: C - 63.90%; H - 5.52%; S - 10.05%

EXAMPLE 4

[2-(2'-Fluoro-4-biphenylyl)-propylsulfinyl]-acetic acid, was prepared analogously to Example 1 from [2-(2'-fluoro-4-biphenylyl)-propylthio]-acetic acid by oxidation with hydrogen peroxide in glacial acetic acid. Yield: 20.2% of theory; m.p 156°–158° C (decomp.; from n-propanol).

Analysis: $C_{17}H_{17}FO_3S$; mol.wt. 320.38 Calculated: C - 63.73%; H - 5.35%; S - 10.01% Found: C - 63.90%; H - 5.44%; S - 9.96%

NMR-spectrum (in deutero dimethyl sulfoxide and deuterochloroform)
$CH_3$ : Doublet at 1.45 ppm (J = 6 Hz),
CH + $CH_2$ at 3.25 ppm,
$CH_2$ : Double doublet at 3.78 ppm (J = 15 Hz).

EXAMPLE 5

[1-(2'-Fluoro-4-biphenylyl)-ethylsulfinyl]-acetic acid methyl ester 800 gm (2.61 mol) of the difficulty soluble diastereoisomer of [1-(2'-fluoro-4-biphenylyl)-ethylsulfinyl]-acetic acid, m.p. 164°–165° C, were suspended in 4 liters of benzene and 125.5 gm (3.92 mol) of methanol, and a solution of 648 gm (3.14 mol) of dicyclohexylcarbodiimide in 650 ml of benzene was added while stirring and cooling at 20°–25° C. The acid dissolved, and dicyclohexylurea precipitated out. The mixture was allowed to stand overnight at room temperature, then the excess of carbodiimide was decomposed by addition of glacial acetic acid, and then 2 liters of water were added, the dicyclohexylurea was suction-filtered off, the organic phase was separated from the filtrate and evaporated in vacuo after drying. The obtained oil (969 gm) was recrystallized from 2.9 liters of isopropanol. Yield: 736 gm (88% of theory); m.p. 75°–77° C.

After a further recrystallization from benzene/cyclohexane = 1/3 the compound had a m.p. of 78°–80° C.

Analysis: $C_{17}H_{17}FO_3S$; mol.wt. 320.36 Calculated: C - 63.73%; H - 5.34%; S - 10.01% Found: C - 63.90%; H - 5.43%; S - 10.21%
NMR-spectrum (in deuterochloroform)
$CH_3$ : Doublet at 1.75 ppm (J = 7.2 Hz)
CH : Quartet at 4.22 ppm ($J_H$, $CH_3$ = 7.2 Hz)
$CH_2$ : Double doublet at 3.48 ppm δτ = about 16 Hz (J=14 Hz)

EXAMPLE 6

[1-(2'-Fluoro-4-biphenylyl)-ethylsulfinyl]-acetic acid methyl ester, was prepared analogous to Example 5 from [1-(2'-fluoro-4-biphenylyl)-ethylsulfinyl]-acetic acid, m.p. 149°–150° C, with methanol and dicyclohexylcarbodiimide in benzene. Yield: 67.4% of theory; m.p. 92°–94° C (cyclohexane/benzene = 3/1).

Analysis: $C_{17}H_{17}FO_3S$; mol.wt. 320.36 Calculated: C - 63.70%; H - 5.34%; S - 10.01% Found: C - 63.90%; H - 5.39%; S - 10.28%
NMR-spectrum (in deuterochloroform)
$CH_3$ : Doublet at 1.8 ppm (J = 7.2 Hz)
CH : Quartet at 4.1 ppm ($J_H$, $CH_3$ = 7.2 Hz)
$CH_2$ : Singlet at 3.31 ppm

EXAMPLE 7

Levorotatory [1-(2'-fluoro-4-biphenylyl)-ethylsulfinyl]-acetic acid methyl ester, was prepared analogous to Example 5 from levorotatory [1-(2'-fluoro-4-biphenylyl)-ethylsulfinyl]-acetic acid ($[\alpha]_D^{20}$ = − 131.5°) with methanol and dicyclohexylcarbodiimide in benzene, followed by purification by column chromatography on silicagel with benzene/ethyl acetate = 1/1. Yield: 87.5% of theory; m.p. 52°–54° C (cyclohexane/benzene = 3'1); $[\alpha]_D^{20}$ = − 179.5° (c = 0.5, methanol).

EXAMPLE 8

Dextrorotatory [1-(2'-fluoro-4-biphenylyl)-ethylsulfinyl]-acetic acid methyl ester, was prepared analogous to Example 5 from dextrorotatory [1-(2'-fluoro-4-biphenylyl)-ethylsulfinyl]-acetic acid ($[\alpha]_D^{20}$ = + 100°) with methanol and dicyclohexylcarbodiimide in benzene, followed by purification by column chromatography on silicagel with benzene/ethyl acetate = 1/1. Yield: 87.5% of theory; oil, $[\alpha]_D^{20}$ = + 112.0° (c = 0.5, methanol), $R_f$-value: 0.3 (silicagel-polygram-plates with benzene/ethyl acetate = 1/1), m.p. 50°–52° C (from cyclohexane/benzene = 4/1).

EXAMPLE 9

[1-(2'-Fluoro-4-biphenylyl)-ethylsulfinyl]-acetic acid isopropyl ester, was prepared analogous to Example 5 from [1-(2'-fluoro-4-biphenylyl)-ethylsulfinyl]-acetic acid, m.p. 164°–165° C, with isopropanol and dicyclohexylcarbodiimide in benzene. Yield: 91% of theory, m.p. 114°–119° C (cyclohexane).

Analysis: $C_{19}H_{21}FO_3S$; mol.wt. 348.44 Calculated: C - 65.50%; H - 6.08%; S - 9.20% Found: C - 65.70%; H - 6.39%; S - 9.00%
NMR-spectrum (in deuterochloroform)
$CH_3$ : Doublet at 1.75 ppm (J = 7 Hz)
CH : Quartet at 4.2 ppm ($J_H$, $CH_3$ = 7 Hz)
$CH_2$ : Double doublet at 3.45 ppm (J = 14 Hz).

EXAMPLE 10

[1-(2'-Fluoro-4-biphenylyl)-ethylsulfinyl]-acetic acid n-butyl ester, was prepared analogous to Example 5 from [1-(2'-fluoro-4-biphenylyl)-ethylsulfinyl]-acetic acid, m.p. 164°–165° C, with n-butanol and dicyclohexylcarbodiimide in benzene, followed by purification by column chromatography on silicagel with cyclohexane/ethyl acetate = 1/1. Yield: 80% of theory; m.p. 74°–75° C (cyclohexane).

Analysis: $C_{20}H_{23}FO_3S$; mol.wt. 362.46 Calculated: C - 66.28%; H - 6.40%; S - 8.84% Found: C - 66.50%; H - 6.51%; S - 8.82%
NMR-spectrum (in deuterochloroform)
$CH_3$ : Doublet at 1.77 ppm (J = 7 Hz)
CH : Quartet at 4.2 ppm (J = 7 Hz)
$CH_2$ : Double doublet at 3.48 ppm (J = 14 Hz)

EXAMPLE 11

[1-(2'-Fluoro-4-biphenylyl)-ethylsulfinyl]-acetic acid isobutyl ester, was prepared analogous to Example 5 from [1-(2'-fluoro-4-biphenylyl)-ethylsulfinyl]-acetic acid, m.p. 164°–165° C, with isobutanol and dicyclohexylcarbodiimide in benzene, followed by purification by column chromatography on silicagel with cyclohexane/ethyl acetate = 1/1. Yield: 77% of theory; m.p. 81°–83° C (cyclohexane)

Analysis: $C_{20}H_{23}FO_3S$; mol.wt. 362.46 Calculated: C - 66.28%; H - 6.40%; S - 8.84% Found: C - 66.20%; H - 6.47%; S - 8.54%
NMR-spectrum (in deuterochloroform)
$CH_3$ : Doublet at 1.75 ppm (J = 7 Hz)
CH : Quartet at 4.22 ppm (J = 7 Hz)
$CH_2$ : Double doublet at 3.48 ppm (J = 14 Hz)

EXAMPLE 12

[1-(2'-Fluoro-4-biphenylyl)-ethylsulfinyl]-acetic acid isoamyl ester, was prepared analogous to Example 5 from [1-(2'-fluoro-4-biphenylyl)-ethylsulfinyl]-acetic acid, m.p. 164°–165° C, with isoamyl alcohol and dicyclohexylcarbodiimide in benzene. Yield: 80.5% of theory; m.p. 74°–76° C (petroleum ether).

Analysis: $C_{21}H_{25}FO_3S$; mol.wt. 376.49 Calculated: C - 67.00%; H - 6.69%; S - 8.52% Found: C - 67.30%; H - 6.86%; S - 8.71%

EXAMPLE 13

[1-(2'-Fluoro-4-biphenylyl)-ethylsulfinyl]-acetic acid n-hexyl ester, was prepared analogous to Example 5 from [1-(2'-fluoro-4-biphenylyl)-ethylsulfinyl]-acetic acid, m.p. 164°–165° C, with n-hexanol and dicyclohexylcarbodiimide in benzene, followed by purification by column chromatography on silicagel with cyclohexane/ethyl acetate = 1/1. Yield: 58% of theory; oil, $R_f$-value: 0.5 (cyclohexane/ethyl acetate = 1/1 on preprepared silicagel plates); m.p. 51°–53° C (from petroleum ether).

Analysis: $C_{22}H_{27}FO_3S$; mol.wt. 390.52 Calculated: C - 67.66%; H - 6.97%; S - 8.21% Found: C - 67.70%; H - 7.17%; S - 8.32%

EXAMPLE 14

[1-(2'-Fluoro-4-biphenylyl)-ethylsulfinyl]-acetic acid benzyl ester, was prepared analogous to Example 5 from [1-(2'-fluoro-4-biphenylyl)-ethylsulfinyl]-acetic acid, m.p. 164°–165° C, with benzyl alcohol and dicyclohexylcarbodiimide in benzene. Yield: 85% of theory; m.p. 123°–125° C (cyclohexane-benzene).

Analysis: $C_{23}H_{21}FO_3S$; mol.wt. 396.48 Calculated: C - 69.67%; H - 5.34%; S - 8.09% Found: C - 69.90%; H - 5.75%; S - 8.05%

EXAMPLE 15

[2-(2'-Fluoro-4-biphenylyl)-propylsulfinyl]-acetic acid methyl ester, was prepared analogous to Example 5 from [2-(2'-Fluoro-4-biphenylyl)-propylsulfinyl]-acetic acid, m.p. 156°–158° C, with methanol and dicyclohexylcarbodiimide in benzene, followed by purification by column chromatography on silicagel with toluene/ethyl acetate = 1/2. Yield: 31.7% of theory; m.p. 127°–129° C (n-butanol).

Analysis: $C_{18}H_{19}FO_3S$; mol.wt. 334.42 Calculated: C - 64.65%; H - 5.73%; S - 9.59% Found: C - 64.90%; H - 5.84%; S - 9.71%

EXAMPLE 16

[1-(2'-Fluoro-4-biphenylyl)-ethylsulfinyl]-acetic acid methyl ester 10 gm (0.033 mol) of [1-(2'-fluoro-4-biphenylyl)ethylsulfinyl]-acetic acid, m.p. 164°–165° C, were suspended in 100 ml of methanol, and 3 ml of phosphorus oxychloride were added dropwise while cooling at 10° C. The mixture was allowed to stand at room temperature for 2 hours, and then the reaction was caused to go to completion by heating to 35° C. The reaction product was precipitated with water and extracted with benzene. The organic extract was evaporated, and the residue was purified by chromatography on silicagel (grain size: 0.5 – 0.2 mm) with benzene/cyclohexane = 1/1. The fractions with an $R_f$-value of 0.4 were combined and evaporated, and the residue (6.0 gm) was recrystallized from cyclohexane/benzene = 3/1. Yield: 4.4 gm (41.5% of theory); m.p. 78°–79° C.

When a corresponding amount of thionyl chloride was used instead of phosphorus oxychloride, the ester was obtained with a yield of 63% of theory.

EXAMPLE 17

[1-(2'-Fluoro-4-biphenylyl)-ethylsulfinyl]-acetic acid ethyl ester, was prepared analogous to Example 16 from [1-(2'-fluoro-4-biphenylyl)-ethylsulfinyl]-acetic acid, m.p. 164°–165° C, with ethanol in the presence of phosphorus oxychloride, followed by purification by column chromatography on silicagel with benzene/cyclohexane = 1/1. Yield: 28.2% of theory; m.p. 84°–85° C (cyclohexane).

Analysis: $C_{18}H_{19}FO_3S$; mol.wt. 334.42 Calculated: C - 64.65%; H - 5.73%; S - 9.59% Found: C - 64.60%; H - 5.80%; S - 9.38%

EXAMPLE 18

[1-(2'-Fluoro-4-biphenylyl)-ethylsulfinyl]-acetic acid n-propyl ester, was prepared analogous to Example 16 from [1-(2'-fluoro-4-biphenylyl)-ethylsulfinyl]-acetic acid, m.p. 164°–165° C, with n-propanol in the presence of thionyl chloride, followed by purification by column chromatography on silicagel with benzene/cyclohexane = 1/1. Yield: 15.5 % of theory; m.p. 55°–57° C (cyclohexane/benzene = 5/1)

Analysis: $C_{19}H_{21}FO_3S$; mol.wt. 348.44 Calculated: C - 65.50%; H - 6.08% Found: C - 65.30%; H - 6.30%

EXAMPLE 19

[1-(2'-Fluoro-4-biphenylyl)-ethylsulfinyl]-acetic acid methyl ester 3 gm (.10 millimols) of [1-(2'-fluoro-4-biphenylyl)-ethylsulfinyl]-acetic acid, m.p. 164°–165° C, were dissolved in 15 ml of dimethyl sulfoxide, 2 gm of potassium carbonate and 1.5 ml of methyl iodide were added, and the mixture was stirred at room temperature for 1 hour. Subsequently, the mixture was diluted with water, hydrochloric acid was added and the reaction product was extracted with ethyl acetate. After washing, drying and evaporating the extract, the residue was recrystallized from isopropanol (10 ml). Yield: 1.4 gm (44% of theory); m.p. 79° C.

EXAMPLE 20

(4-Biphenylyl-methylsulfinyl)-acetic acid methyl ester 0.05 mol of 30% hydrogen peroxide were added dropwise over a period of 30 minutes to a solution of 12.8 gm (0.047 mol) of (4-biphenylyl-methylthio)-acetic acid methyl ester in 60 ml of glacial acetic acid at 10° to 15° C. The mixture was allowed to stand at room temperature overnight, and the reaction product was precipitated with water, dried and purified by column chromatography on 800 gm of silicagel (grain size: 0.05 – 0.2 mm) using ethyl acetate as the eluant. Yield: 11.2 gm (83% of theory); m.p. 151°–152° C (from benzene).

Analysis: $C_{16}H_{16}O_3S$; mol.wt. 288.37 Calculated: C - 66.64%; H - 5.59%; S - 11.12% Found: C - 66.90%; H - 5.79%; S - 11.38%

NMR-spectrum (in deuterochloroform)
$CH_2$ : Double doublet at 3.6 ppm (J = 14 Hz)
$CH_2$ : Double doublet at 4.2 ppm (J = 14 Hz)

EXAMPLE 21

[2-(4-Biphenylyl)-ethylsulfinyl]-acetic acid methyl ester, was prepared analogous to Example 20 from [2-(4-biphenylyl)ethylthio]-acetic acid methyl ester and hydrogen peroxide in glacial acetic acid, followed by purification by column chromatography on silicagel with benzene/ethyl acetate/methanol = 8/4/1. Yield: 43.3% of theory; m.p. 85°–86° C (benzene/cyclohexane = 1/1).

Analysis: $C_{17}H_{18}O_3S$; mol. wt. 302.40 Calculated: C - 67.52%; H - 6.00%; S - 10.60% Found: C - 67.80%; H - 6.03%; S - 10.50%

EXAMPLE 22

[1-(4-Biphenylyl)-ethylsulfinyl]-acetic acid methyl ester, was prepared analogous to Example 20 from [1-(4-biphenylyl)-ethylthio]-actic acid methyl ester and hydrogen peroxide in glacial acetic acid. Yield: 31% of theory; m.p. 86–87° C (benzene/cyclohexane = 1/3)

Analysis: $C_{17}H_{18}O_3S$; mol.wt. 302.40 Calculated: C - 67.52%; H - 6.00%; S - 10.60 Found: C - 67.60%; H - 5.97%; S - 10.63%

NMR-spectrum (in deuterochloroform)
$CH_3$ : Doublet at 1.75 ppm (J = 7 Hz)
CH : Quartet at 4.2 ppm (J = 7 Hz)
$CH_2$ : Double doublet at 3.45 ppm (J = 14 Hz)

EXAMPLE 23

[1-(2'-Fluoro-4-biphenylyl)-ethylusulfinyl]-acetic acid methyl ester, was prepared analogous to Example 20 from [1-(2'-fluoro-4-biphenylyl)-ethylthio]-acetic acid methyl ester by oxidation with hydrogen peroxide in glacial acetic acid. The separation of the two diastereoisomeric esters was carried out by column chromatography on silicagel (grain size: 0.05 – 0.2 mm) with a ratio of substance/silicagel = 1.60; eluant: cyclohexane/ethyl acetate = 1/4). Yield: 12% of theory of one diastereoisomer of [1-(2'-fluoro-4-biphenylyl)-ethylsulfinyl]-acetic acid methyl ester, m.p. 92°–94° C, and 14% of theory of the other diastereoisomer of [1-(2'-fluoro-4-biphenylyl)-ethylsulfinyl]-acetic acid methyl ester, m.p. 77°–78° C.

EXAMPLE 24

α,α-Dimethyl-(2'-fluoro-4-biphenylyl)-methylsulfinyl-acetic acid methyl ester, was prepared analogous to Example 20 from α,α-dimethyl-(2'-fluoro-4-biphenylyl)-methylthio-acetic acid methyl ester by oxidation with hydrogen peroxide in glacial acetic acid. Yield: 66% of theory; oil, $R_f$-valve: 0.3 (benzene/ethyl acetate = 2/1 on silicagel-polygram-plates).

Analysis: $C_{18}H_{19}FO_3S$; mol.wt. 334.42 Calculated: C - 64.65%; H - 5.73%; S - 9.59% Found: C - 64.70%; H - 5.97%; S - 9.80%

EXAMPLE 25

[1-(2'-Fluoro-4-biphenylyl)-propylsulfinyl]-acetic acid methyl ester, was prepared analogous to Example 20 from [1-(2'-fluoro-4-biphenylyl)-propylthio]-acetic acid methyl ester by oxidation with hydrogen peroxide in glacial acetic acid, followed by purification by column chromatography on silicagel with benzene/ethyl acetate = 1/1. Yield: 94.6% of theory; oil, $R_f$-value: 0.4 + 0.5 with benzene/ethyl acetate = 1/1 silicagel-polygram (double spot).

Analysis: $C_{18}H_{19}FO_3S$; mol.wt. 334.42 Calculated: C - 64.65%; H - 5.73%; S - 9.59% Found: C - 65.00%; H - 5.88%; S - 9.35%

EXAMPLE 26

[4-(4-Biphenylyl)-butylsulfinyl]-acetic acid methyl ester, was prepared analogous to Example 20 from [4-(4-biphenylyl)-butylthio]-acetic acid methyl ester by oxidation with hydrogen peroxide in glacial acetic acid. Yield: 72% of theory; m.p. 77°–78° C (benzene/cyclohexane =0 1/2) Analysis: $C_{19}H_{22}O_3S$; mol.wt. 330.45 Calculated: C - 69.06%; H - 6.71%; S - 9.70% Found: C - 69.10%; H - 6.75%; S - 9.85%

EXAMPLE 27 8

4-(2'-Fluoro-4-biphenylyl)-butylsulfinyl]-acetic acid methyl ester, was prepared analogous to Example 20 from [4-(2'-fluor-4-biphenylyl)-butylthio]-acetic acid methyl ester by oxidation with hydrogen peroxide in glacial acetic acid. Yield: 91% of theory; oil, $R_f$-value: 0.32 (benzene/ethyl acetate =2/1 on silicagel-polygram-plates).

Analysis: $C_{19}H_{21}FO_3S$; mol.wt. 348.44 Calculated: C - 65.50%; H - 6.07%; S - 9.20% Found: C - 65.30% H - 6.17%; S - 9.30%

EXAMPLE 28

[3-(4-Biphenylyl)-butylsulfinyl]acetic acid methyl ester, was prepared analogous to Example 20 from [3-(4-biphenylyl)-butylthio]-acetic acid methyl ester by oxidation with hydrogen peroxide in glacial acetic acid. Yield: 97% of theory; oil; $R_f$-value: 0.32 (ethyl acetate on silicagel-polygram-plates).

Analysis; $C_{19}H_{22}O_3S$; mol.wt. 330.45 Calculated: C - 69.06%; H - 6.71%; S - 9.70% Found: C - 69.00%; H - 6.92%; S - 9.40%

EXAMPLE 29

[3-(2'-Fluoro-4-biphenylyl)-butylsulfinyl]-acetic acid methyl ester, was prepared analogous to Example 20 from [3-(2'- fluoro-4-biphenylyl)-butylthio]-acetic acid methyl ester by oxidation with hydrogen peroxide in glacial acetic acid. Yield: 93% of theory; oil, $R_f$-value: 0.42 (benzene/ethyl acetic = 2/1).

Analysis: $C_{19}H_{21}FO_3S$; mol.wt. 348.44 Calculated: C - 65.50%; H - 6.07%; S - 9.20% Found: C - 65.20%; H - 6.17%; S - 9.07%

EXAMPLE 30

[1-(2'-Fluoro-4-biphenylyl)-ethylsulfinyl]-acetic acid methyl ester 306 mgm (1millimol) of [1-(2'-fluoro-4-biphenylyl)-ethylsulfinyl]-acetic acid and 0.15 ml of triethylamine were dissolved in 2 ml of chloroform, and 0.15 ml of chloroformic acid methyl ester was added to the solution at room temperature. After 30 minutes of standing, the mixture was washed with water, dried and evaporated, and the residue was recrystallized from 1 ml. of isopropanol. Yield: 200 mgm (62.5% of theory); m.p. 75°–78° C.

EXAMPLE 31

[1-(2'-Fluoro-4-biphenylyl)-ethyl]-methylsulfoxide, was prepared analogous to Example 20 from [1-(2'-fluoro-4-biphenylyl)-ethylthio]-methylether by oxidation with hydrogen peroxide in glacial acetic acid. Yield: 95% of theory; oil, $R_f$-value: 0.6 (benzene/ethyl acetate/methanol = 8/4/2 on silica-gel-polygram-plates).

Analysis: $C_{15}H_{15}FOS$; mol.wt. 262.35 Calculated: C - 68.68%; H - 5.76%; S - 12.22% Found: C - 68.80%; H - 5.88%; S - 11.95%

EXAMPLE 32

[1-(2'-Fluoro-4-biphenylyl)-ethylsulfinyl]-acetic acid methyl ester 1.5 gm (50 millimols) of [1-(2'-fluoro-4-biphenylyl)-ethylsulfinyl]-acetic acid, m.p. 164°–165° C, were dissolved in 3 ml of methanol and 1.2 ml of 2,2-dimethoxypropane, 100 mgm of p-toluenesulfonic acid were added to the solution, and the mixture was allowed to stand for 12 days at room temperature. Then, water was added and the ester was extracted with toluene. The organic extract was washed with water, dried and evaporated, and the residue was purified by chromatography on 75 gm of silicagel (grain size 0.05 – 0.2 mm) with cyclohexane/ethyl acetate = 1/4. The combined ester -containing fractions were evaporated, and the residue was recrystallized from 3 ml of isopropanol. Yield: 800 mgm (50% of theory); m.p. 77-79° C.

EXAMPLE 33

[1-(2'-Fluoro-4-biphenylyl)-ethylsulfinyl]-acetic acid-n-butyl ester 1.5 gm (5 millimols) of [1-(2'-fluoro-4-biphenylyl)-ethylsulfinyl]-acetic acid, m.p. 164° – 165° C, were stirred with 1.05 gm of potassium carbonate and 0.9 ml of n-butyl bromide in 15 ml of dimethyl sulfoxide for 60 hours. The mixture was subsequently diluted with water, and the reaction product was extracted with toluene. After washing, drying and evaporating the extract, the residue (1.7 gm) was recrystallized from cyclohexane. Yield: 1.2 gm (67% of theory); m.p.: 72° – 74° C.

EXAMPLE 34

[1-(2'-Fluoro-4-biphenylyl)-ethylsulfinyl]-acetic acid-n-butyl ester, was prepared analogous to Example 33 from [1-(2'-fluoro-4-biphenylyl)-ethylsulfinyl]-acetic acid, m.p. 164° – 165° C, and tri-n-butyl-phosphate in the presence of calcium oxide in dimethyl sulfoxide. Yield: 58% of theory; m.p.: 71 – 73° C.

EXAMPLE 35

[1-(2'-Fluoro-4-biphenylyl)-ethylsulfinyl]-acetic acid methyl ester

A solution of 320 mgm (7.6 millimols) of diazomethane (prepared from 2.14 gm of p-toluenesulfonylmethylnitrosoamide in 30 ml of ether and 0.4 gm of potassium hydroxide in 10 ml of 96% ethanol and subsequent distillation) was added, while stirring, to a suspension of 2.3 gm (7.5 millimols) of [1-(2'-fluoro-4-biphenylyl)-ethylsulfinyl]-acetic acid (m.p.: 164° – 165° C) in 20 ml of ether. The acid dissolved, accompanied by nitrogen evaluation. After the reaction was finished, the mixture was evaporated, and the residue was recrystallized from benzene cyclohexane (1/5). Yield: 2.0 gm (83.5% of theory); m.p.: 75° – 77° C.

EXAMPLE 36

[1-(2'-Fluoro-4-biphenylyl)-ethylsulfinyl]-acetic acid ethyl ester, was prepared analogous to Example 35 from [1-(2'-fluoro-4-biphenylyl)-ethylsulfinyl]-acetic acid, m.p. 164° – 165° C, and diazoethane in ether. Yield: 78% of theory; m.p.: 82° – 84° C.

EXAMPLE 37

[1-(2'-Fluoro-4-biphenylyl)-ethylsulfinyl]-acetic acid methyl ester 1.1 gm (3 millimols) of tetrabutylammonium iodide and 3.06 gm (10 millimols) of [1-(2'-fluoro-4-biphenylyl)-ethylsulfinyl]-acetic acid (m.p. 164° – 165° C) were added to a solution of 730 mgm (13 millimols) of potassium hydroxide in 20 ml of water, then 20 ml of chloroform and 2 ml of methyl iodide were added, and the mixture was stirred at room temperature for 10 hours. Afterwards, the organic phase was separated from the neutral aqueous phase, washed with dilute hydrochloric acid and then with water, dried and evaporated. The residue (3.6 gm) was purified by chromatography on 100 gm of silicagel (grain size: 0.05 – 0.2 mm) with cyclohexane ethyl acetate = 1/4. After evaporation of the combined fractions with an $R_f$-value of 0.4 and recrystallization of the residue from isopropanol, 1.7 gm (53% of theory) of the title compound m.p. 75° – 77° C were obtained.

EXAMPLE 38

[1-(2'-Fluoro-4-biphenylyl)-ethylsulfinyl]acetic acid methyl ester, was prepared analogous to Example 33 from [1-(2'-fluoro-4-biphenylyl)-ethylsulfinyl]-acetic acid, m.p. 164° – 165° C, and dimethyl sulfate in the presence of potassium carbonate in acetone. Yield: 68% of theory; m.p.: 75° – 77° C.

EXAMPLE 39

[1-(2'-Chloro-4-biphenyl)-ethylsulfinyl]-acetic acid 50 gm (0.163 mol) of [1-(2'-chloro-4-biphenylyl)-ethylthio]-acetic acid were suspended in 163 ml of glacial acetic acid and 16.0 gm (0.171 mol) of 36.3% hydrogen peroxide were added dropwise to the suspension at 10° C while vigorously stirring. Afterwards, the mixture was allowed to stand overnight at room temperature, during which time the starting compound dissolved. Subsequently, 500 ml of water were added, the reaction product was extracted with ethyl acetate, and the organic solvent was removed from the extract in vacuo, leaving 45.1 gm (85% of theory) of the title compound, m.p. 144° – 147° C (from ethyl acetate).

Analysis: $C_{16}H_{15}ClO_3S$; mol. wt. 322.82 Calculated: C-59.53%; H-4.68%; Cl-10.98%; S-9.93% Found: C-59.50%; H-4.89%; Cl-10.98%; S-9.76%

$CH_3$: Doublet at 1.8 ppm
CH : Quartet at 4.25 ppm ($J_{H,CH_3}$ = 7 Hz)
$CH_2$: Doublet at 3.5 ppm

EXAMPLE 40

[1-(2'-Chloro-4-biphenylyl)-ethylsulfinyl]-acetic acid methyl ester

A solution of 19.9 gm (0.059 mol) of [1-(2'-chloro-4-biphenylyl)-ethylsulfinyl]-acetic acid and 12.5 gm (0.088 mol) of methyl iodide in 120 ml of dry dimethyl sulfoxide was admixed with 12.2 gm (0.088 mol) of dry potassium carbonate, and the mixture was stirred at room temperature for 19 hours. The crude reaction product was precipitated with water and extracted with ethyl acetate (yield: 23.1. gm). For purification, the obtained crude product was purified by chromatography on 1200 gm of silicagel with cyclohexane ethyl acetate = 1/1. The combined fractions with an $R_f$-value of 0.23 (on carrier 2) were combined and evaporated, leaving 6.2 gm (31.2% of theory) of the title compound; oil, $R_f$-value: 0.23 on carrier 1 with cyclohexane/ethyl acetate = 1/1.

Analysis: $C_{17}H_{17}ClO_3S$; mol.wt. 336.85 Calculated: C-60.62%; H-5.09%; Cl-10.53%; S-9.52% Found: C-60.90%; H-5.66%; Cl- 9.68%; S-8.54%

EXAMPLE 41

[1-(2'-Chloro-4-biphenylyl)-ethylsulfinyl]-acetic acid ethyl ester, was prepared analogous to Example 40 from [1-(2'-chloro-4-biphenylyl)-ethylsulfinyl]-acetic acid and ethyl iodide in dimethyl sulfoxide in the presence of potassium carbonate. The diastereoisomers were separated by column chromatography on silicagel with cyclohexane/ethyl acetate = 1/1.

1st Diastereoisomer:
Oil. $R_f$-value: 0.4 on carrier 2 with cyclohexane/ethyl acetate = 1/1; yield: 11% of theory.
Analysis: $C_{18}H_{19}ClO_3S$; mol.wt. 350.86 Calculated: C-61.62%; H-5.46%; Cl-10.12%; S-9.14% Found: C-61.90%; H-5.79%; Cl-9.14%; S-8/31%
NMR-spectrum (in $CDCl_3$):
$CH_2$ : Singlet 3.3 ppm 2nd Diastereoisomer:
Crystals, m.p. 81°–82° C (from cyclohexane)
Yield: 62.8% of theory
$R_f$-value: 0.3 on carrier 2 with cyclohexane/ethyl acetate=1/1
Analysis: $C_{18}H_{19}ClO_3S$; mol.wt. 350.86 Calculates: C-61.62%; H-5.46%; Cl-10.12%; S-9.14% Found: C-61.50%; H-5.45%; Cl-10.05%; S-8.94%
NMR-spectrum (in $CDCl_3$):
$CH_3$ : Doublet at 1.8 ppm (J = 7 Hz)
CH : Quartet at 4.25 ppm (J = 7 Hz)
$CH_2$ : Double doublet at 3.5 ppm (J = 14 Hz)

EXAMPLE 42

[1-(2-Fluoro-4-biphenylyl)-ethylsulfinyl]-acetic acid, was prepared analogous to Example 39 from [1-

(2-fluoro-4-biphenylyl)-ethylthio]-acetic acid by oxidation with hydrogen peroxide in glacial acetic acid. The diastereoisomers were separated on the basis of their different solubility in glacial acetic acid.

Difficultly soluble isomer:
Yield: 59% of theory; m.p. 161°–163° C (decomp.); from glacial acetic acid.
Analysis: $C_{16}H_{15}FO_3S$; mol.wt. 306.37 Calculated: C - 62.73%; H - 4.94%; S - 10.47% Found: C - 63.00%; H - 5.07%; S - 10.71%
NMR-spectrum (in $CDCl_3$-$CD_3OD$):
$CH_3$ : Doublet at 1.8 ppm (J = 7 Hz)
CH : Quartet at 4.3 ppm (J = 7 Hz)
$CH_2$ : slightly split doublet at 3.55 ppm Easily soluble isomer:
Yield: 16% of theory; m.p. 151°–153° C (decomp.); from ethyl acetate
Analysis: $C_{16}H_{15}FO_3S$; mol.wt. 306.37 Calculated: C - 62.73%; H - 4.94%; S - 10.47% Found: C - 62.40%; H - 4.94%; S - 10.35%
NMR-spectrum (in $CDCl_3$-$CD_3OD$):
$CH_3$ : Doublet at 1.8 ppm (J = 7 Hz)
CH : Quartet at 4.15 ppm (J = 7 Hz)
$CH_2$ : Doublet at 3.5 ppm (J = 8 Hz)

EXAMPLE 43

[1-(2-Fluoro-4-biphenylyl)-ethylsulfinyl]-acetic acid methyl ester

A solution of 1.53 gm (5 millimols) of [1-(2-fluoro-4-biphenylyl)-ethylsulfinyl]-acetic acid, m.p. 161°–163° C, in 15 ml of benzene was admixed with 0.24 gm (7.5 millimols) of methanol, and then a solution of 1.25 gm (6 millimols) of dicyclohexyl-carbodiimide in 5 ml of benzene was added. After stirring for one hour, the precipitated dicyclohexylurea was suction-filtered off, the filtrate was evaporated, and the residue was purified by chromatography on 300 gm of silicagel with cyclohexane/ethyl acetate = 1/4. Yield: 1.4 gm (87.6% of theory); oil, $R_f$-value: 0.5 on carrier 1 with cyclohexane/ethyl acetate = 1/4.
Analysis: $C_{17}H_{17}FO_3S$; mol.wt. 320.36 Calculated: C-63.73%; H-5.34%; S-10.01% Found: C-63.70%; H-5.58%; S-10.25%
NMR-spectrum ($CDCl_3$): $CH_2$ : Doublet at 3.5 ppm

EXAMPLE 44

[1-(2-Fluoro-4-biphenylyl)-ethylsulfinyl]-acetic acid methyl ester, was prepared analogous to Example 43 from [1-(2-fluoro-4-biphenylyl)-ethylsulfinyl]-acetic acid, m.p. 151°–153° C; yield: 44% of theory; m.p. 88°–92° C (from cyclohexane/benzene = 4/1)
Analysis: $C_{17}H_{17}FO_3S$; mol.wt. 320.36 Calculated: C-63.73%; H-5.34%; S-10.01% Found: C-63.80%; H-5.72%; S- 9.84%

EXAMPLE 45

[1-(2'-Fluoro-4-biphenylyl)-ethylsulfinyl]-acetic acid crotyl ester, was prepared analogous to Example 40 from [1-(2'-fluoro-4-biphenylyl)-ethylsulfinyl]-acetic acid, m.p. 164°–165° C, and crotyl chloride in dimethylsulfoxide in the presence of potassium carbonate. Yield: 83.5% of theory; oil, $R_f$-value: 0.3 on carrier 2 with cyclohexane/ethyl acetate = 3/2.
Analysis: $C_{20}H_{21}FO_3S$; mol.wt. 360.44 Calculated: C-66.65%; H-5.87%; S-8.89% Found: C-66.80%; H-6.00%; S-9.11%
NMR-spectrum (in $CDCl_3$): $CH_2$ - Double doublet at 1.5 ppm (J = 13 Hz)

EXAMPLE 46

[1-(2'-Fluoro-4-biphenylyl)-ethylsulfinyl]-acetic acid-(2-methoxy-ethyl)-ester

A suspension of 5.0 gm (16.4 millimols) of [1-(2'-fluoro-4-biphenylyl)-ethylsulfinyl]-acetic acid, m.p. 164°–165° C, in 50 ml of dry tetrahydrofuran was admixed with 2.92 gm (18.1 millimols) of carbonyldiimidazole, whereupon the acid dissolved and carbon dioxide was given off. After one hour, 1.37 gm (18.1 millimols) of glycol monomethyl ether were added, and the mixture was allowed to stand for 2 hours. For isolation of the reaction product, the mixture was evaporated, and the residue was distributed between dilute hydrochloric acid and ethyl acetate, and the organic solution was purified by chromatography on 180 gm of silicagel with cyclohexane/ethyl acetate = 1/4. For further purification, the product mixture was recrystalized from cyclohexane/ethyl acetate = 4/1. Yield: 3.8 gm (63.8% of theory); m.p. 65°–67° C.
Analysis: $C_{19}H_{21}FO_4S$; mol.wt. 364.43 Calculated: C-62.62%; H-5.81%; S-8.80% Found: C-62.50%; H-5.85%; S-9.01%

EXAMPLE 47

[1-(2'-Fluoro-4-biphenylyl)-ethylsulfinyl]-acetic acid allyl ester, was prepared analogous to Example 46 from [1-(2'-fluoro-4-biphenylyl)-ethylsulfinyl]-acetic acid, m.p. 164°–165° C, and allyl alcohol, followed by purification by column chromatography with cyclohexane/ethyl acetate = 1/1. Yield: 67.3% of theory; m.p. 59°–61° C (cyclohexane/ethyl acetate=9/1)
Analysis: $C_{19}H_{19}FO_3S$; mol. wt. 346.42 Calculated: C-65.88%; H-5.53%; S-9.25%; Found: C-66.00%; H-5.72%; S-9.45%

EXAMPLE 48

[1-(2'-Fluoro-4-biphenylyl)-ethylsulfinyl]-acetic acid (2-pyridylmethyl) ester, was prepared analogous to Example 46 from [1-(2'-fluoro-4-biphenylyl)-ethylsulfinyl]-acetic acid, m.p. 164°–165° C, and pyridyl-(2)-methanol. Yield: 75.5% of theory; m.p. 92°–94° C (cyclohexane/ethyl acetate = 1/1)
Analysis: $C_{22}H_{20}FNO_3S$; mol.wt. 397.47 Calculated: C-$_{66.48}$%; H-5.07%; S-8.07% Found: C-66.80%; H-5.13%; S-8.30%

Example 49

[1-(2'-Fluoro-4-biphenylyl)-ethylsulfinyl]-acetic acid (3-pyridylmethyl) ester, was prepared analogous to Example 46 from [1-(2'-fluoro-4-biphenylyl)-ethylsulfinyl]-acetic acid, m.p. 164°–165° C, and pyridyl-(3)-methanol. Yield: 80.3% of theory; m.p. 94°–96° C (cyclohexane/ethyl acetate = 2/1)
Analysis: $C_{22}H_{20}FNO_3S$; mol.wt. 397.47 Calculated: C-66.48%; H-5.07%; N-3.52%; S-8.07% Found: C-66.80%; H-5.18%; N-3.41%; S-8.17%

EXAMPLE 50

[1-(2'-Fluoro-4-biphenylyl)-ethylsulfinyl]-acetic acid phenyl ester, was prepared analogous to Example 46 from [1-(2'-fluoro-4-biphenylyl)-ethylsulfinyl]-acetic acid, m.p. 164°–165° C, and phenol. Yield: 46% of theory; m.p. 116°–118° C (cyclohexane/ethyl acetate = 4/1)
Analysis: $C_{22}H_{19}FO_3S$; mol.wt. 382.46 Calculated: C-69.09%; H-5.01%; S-8.38% Found: C-69.25%; H-5.21%; S-8.55%

EXAMPLE 51

[1-(2'-Fluoro-4-biphenylyl)-ethylsulfinyl]-acetic acid amide 2.4 gm (31.5 millimols) of hydrogen peroxide were added dropwise to 8.7 gm (30 millimol) of [1-(2'-fluoro-4-biphenylyl)-ethylthio]-acetic acid amide in 30 ml of glacial acetic acid. After 1¼ hours water was added, and the crystalline precipitate was suction-filtered off, washed with water and dried. The two diastereoisomers were separated by fractional crystallization from toluene.

a. Difficulty soluble isomer

M.p. 177°-179° C (decomp.); yield: 59% of theory.

Analysis: $C_{16}H_{16}FNO_2S$; mol.wt. 305.36 Calculated: C-62.93%; H-5.28%; N-4.59%; S-10.50% Found: C-62.80%; H-5.35%; N-4.60%; S-10.72%

NMR-spectrum (in $CDCl_3$-$CD_3OD$):
$CH_3$ : Doublet at 1.75 ppm (J = 7 Hz)
CH : Quartet at 4.25 ppm (J = 7 Hz)
$CH_2$ : Double doublet at 3.4 ppm (J = 14 Hz)

b. Easily soluble isomer

M.P. 131-133° C; yield: 14.8% of theory.

Analysis: $C_{16}H_{16}FNO_2S$; mol.wt. 305.36 Calculated: C-62.93%; H-5.28%; N-4.59%; S-10.50% Found: C-63.00%; H-5.32%; N-4.63%; S-10.50%

NMR-spectrum (in CDCl -$CD_3OD$):
$CH_3$ : Doublet at 1.75 ppm (J = 7Hz)
CH : Quartet at 4.15 ppm
$CH_2$ : Singlet at 3.3 ppm

EXAMPLE 52

[1-(2'-Fluoro-4-biphenylyl)-ethylsulfinyl]-acetic acid methyl amid, was prepared analogous to Example 51 from [1-(2'-fluoro-4-biphenylyl)-ethylthio]-acetic acid methyl amide by oxidation with hydrogen peroxide in glacial acetic acid. The two diastereoisomers were separated by fractional crystallization from toluene and purified by column chromatography on silica-gel with toluene/ethyl acetate/methanol = 8/4/1.

a. Difficulty soluble isomer

M.P. 136°-139° C (from toluene/cyclohexane); yield: 61% of theory

Analysis: $C_{17}H_{18}FNO_2S$; mol.wt. 319.41 Calculated: C-63.93%; H-5.68%; N-4.39%; S-10.04% Found: C-64.00%; H-5.72%; N-4.27%; S-10.15% NMR-spectrum (in $CDCl_3$): $CH_2$ : Double doublet at 3.25 ppm ($\delta\tau = 36$ Hz, J = 14 Hz)

b. Easily soluble isomer

M.p. 126-136° C; yield: 30% of theory

Analysis: $C_{17}H_{18}FNO_2S$; mol.wt. 319.41 Calculated: C-63.93%; H-5.68%; N-4.39%; S-10.04% Found: C-64.00%; H-5.71%; N-4.59%; S-10.07%

NMR-spectrum (in $CDCl_3$):
$CH_2$ : Double doublet at 3.25 ppm ($\delta\tau = 7$ Hz, J = 3 Hz)

EXAMPLE 53

[1-(2'-Fluoro-4-biphenylyl)-ethylsulfinyl]-acetic acid methylamide
Difficulty soluble isomer 3.06 gm (10 millimols) of [1-(2'-fluoro-4-biphenylyl)-ethylsulfinyl]-acetic acid of m.p. 164-165° C, were suspended in 50 ml of tetrahydrofuran, and 1.95 gm (12 millimols) of carbonyl-diimidazole were added to the suspension. The acid dissolved, accompanied by carbon dioxide evolution. After 20 minutes, dry methylamine was introduced until the mixture was saturated. After another hour, the mixture was evaporated in vacuo, and the residue was taken up in a mixture of dilute hydrochloric acid and ether. 2.55 gm (80% of theory) of the title compound, m.p. 136-137° C, were obtained from the ether phase after washing, drying, evaporation and recrystallization from toleuen/cyclohexane = 1/1.

EXAMPLE 54

The easily soluble isomer of [1-(2'-fluoro-4-biphenylyl)-ethylsulfinyl]-acetic acid methylamide, was prepared analogous to Example 53 from [1-(2'-fluoro-4-biphenylyl)-ethylsulfinyl]-acetic acid, m.p. 149°-150° C, carbonyldiimidazole and methylamine. Yield: 50% of theory; m.p. 136°-139° C (toluene/cyclohexane = 1/1).

EXAMPLE 55

The difficultly soluble isomer of [1-(2'-fluoro-4-biphenylyl)-ethylsulfinyl]-acetic acid dimethylamide was prepared analogous to Example 51 from [1-(2'-fluoro-4-biphenylyl)-ethylthio]-acetic acid dimethylamide by oxidation with hydrogen peroxide in glacial acetic acid. Yield: 57% of theory; m.p. 131°-133° C (from toluene)

Analysis: $C_{18}H_{20}FNO_2S$; mol.wt. 333.42 Calculated: C-64.84%; H-6.05%; N-4.20%; S-9.62% Found: C-65.05%; H-6.36%; N-4.13%; S-9.62%

NMR-spectrum (in $CDCl_3$):
$CH_2$ : Double doublet at 3.63 ppm ($\delta\tau = 32$ Hz, J = 14 Hz)

EXAMPLE 56

A mixture of the diastereoisomers of [1-(2'-fluoro-4-biphenylyl)-ethylsulfinyl]-acetic acid piperidide, was prepared analogous to Example 51 from [1-(2'-fluoro-4-biphenylyl)-ethylthio]-acetic acid piperidide by oxidation with hydrogen peroxide in glacial acetic acid, followed by purification by column chromatography on silicagel with toluene/ethyl acetate/methanol = 8/4/1. Yield: 99% of theory; oil, $R_f$-value: 0.2 and 0.3 on carrier 1 with toluene/ethyl acetate/methanol = 8/4/1.

Analysis: $C_{20}H_{24}FNO_2S$; mol.wt. 373.49 Calculated: NC - 3.75%; S - 8.58% Found: NC - 3.32%; S - 8.35%

EXAMPLE 57

A mixture of the diastereoisomers of [1-(2'-fluoro-4-biphenylyl)-ethylsulfinyl]-acetic acid morpholide, was prepared analogous to Example 51 from [1-(2'-fluoro-4-biphenylyl)-ethylthio]-acetic acid morpholide by oxidation with hydrogen peroxide in glacial acetic acid, followed by purification by filtration through silicagel. Yield: 94% of theory; oil, $R_f$-values: 0.3 and 0.4 on carrier 1 with toluene/ethyl acetate/methanol = 8/4/1.

Analysis: $C_{20}H_{22}FNO_3S$; mol.wt. 375.47 Calculated: N - 3.73%; S - 8.54% Found: N - 3.57%; S - 8.38%

EXAMPLE 58

[1-(2'-Fluoro-4-biphenylyl)-ethylsulfinyl]-acetic acid (1-oxido-thiomorpholide), was prepared analogous to Example 51 from [1-(2'-fluoro-4-biphenylyl)-ethylthio]-acetic acid thiomorpholide by oxidation with hydrogen peroxide in glacial acetic acid. Yield: 51.4% of theory; m.p. 183°-185° C (from ethanol)

Analysis: $C_{20}H_{22}FNO_3S_2$; mol.wt. 407.54 Calculated: C-58.94%; H-5.44%; N-3.44%; S-15.74% Found: C-59.10%; H-5.46%; N-3.39%; S-15.65%

EXAMPLE 59

[1-(2'-Chloro-4-biphenylyl)-ethylsulfinyl]-acetic acid amide, was prepared analogous to Example 51 from [1-(2'-chloro-4-biphenylyl)-ethylthio]-acetic acid amide by oxidation with hydrogen peroxide in glacial acetic acid. Yield: 60% of theory; m.p. 190° C (decomp.). (from n-propanol).

Analysis: $C_{16}H_{16}ClNO_2S$; mol.wt. 321.84 Calculated: C-59.71%; H-5.01%; N-4.35%; Cl-11.02%; S- 9.96% Found: C-59.50%; H-5.02%; N-4.28%; Cl-11.08%; S-10.05%

EXAMPLE 60

A mixture of the diastereoisomers of [1-(2'-chloro-4-biphenylyl)-ethylsulfinyl]-acetic acid piperidide, was prepared analogous to Example 51 from [1-(2'-chloro-4-biphenylyl)-ethylthio]-acetic acid piperidide by oxidation with hydrogen peroxide in glacial acetic acid, followed by purification by filtration through silicagel. Yield: 96% of theory; oil, $R_f$-value: 0.3 and 0.4 on carrier 1 with toluene/ethyl acetate/methanol = 8/4/1.

Analysis $C_{21}H_{24}ClNO_2S$; mol.wt. 389.95 Calculated: C-64.68%; H-6.20%; N-3.59%; Cl-9.09%; S-8.22% Found: C-65.70%; H-6.39%; N-3.44%; Cl-8.87%; S-8.30%

EXAMPLE 61

A mixture of the diastereoisomers of [1-(2'-chloro-4-biphenylyl)-ethylsulfinyl]-acetic acid morpholide, was prepared analogous to Example 51 from [1-(2'-chloro-4-biphenylyl)-ethylthio]-acetic acid morpholide by oxidation with hydrogen peroxide in glacial acetic acid, followed by purification by filtration through silicagel. Yield: 87% of theory; oil, $R_f$-value: 0.3 and 0.35 on carrier 1 with toluene/ethylacetate/methanol = 8/4/1.

Analysis: $C_{20}H_{22}ClNO_3S$; mol.wt. 391.93 Calculated: C-61.29%; H-5.66%; N-3.57%; Cl-9.05%; S-8.18% Found: C-61.60%; H-5.86%; N-3.44%; Cl-9.00%; S-8.42%

EXAMPLE 62

Oxidation of [1-(2'-fluoro-4-biphenylyl)-ethylthio]-acetic acid into [1-(2'-fluoro-4-biphenylyl)-ethylsulfinyl]-acetic acid 1.45 gm (5 millimols) each of [1-(2'-fluoro-4-biphenylyl)-ethylthio]-acetic acid were added to the amount of solvent indicated in the following table, and the oxidizing agent was added. After the reaction, the mixture was diluted with water and, if no alkaline solvent was used, acidified. The mixture of the diastereoisomers was suction-filtered off and dried.

The ratio of the two diastereoisomers in the product was determined after thin-layer chromatographic separation of their methyl esters by evaluation of the spot intensities under the UV-lamp.

The esterification was effected in dimethyl sulfoxide with methyl iodide in the presence of potassium carbonate. In the table A = [1-(2'-fluoro-4-biphenylyl)-ethylsulfinyl]-acetic acid methyl ester, m.p. 78°–80° C, and B = [1-(2'-fluoro-4-biphenylyl)-ethylsulfinyl]-acetic acid methyl ester, m.p. 92°–94° C.

| Solvent | Oxidizing agent | Reaction time | Reaction temperature | Yield of diastereo-isomeric mixture | Percent ratio A/B |
|---|---|---|---|---|---|
| 25 ml of 80% pyridine | 2.0 gm of iodobenzene dichloride | 45 minutes | 0 – 10° C | 100% | 50 : 50 |
| 30 ml of methanol | 1.6 gm (7.5 mmols) of sodium iodate in 10 ml of water | 2 hours | 25° C | 90% | 70 : 30 |
| 0.56 gm of sodium carbonate in 30 ml of water | 0.49 gm (5.25 mmols) of 36.3% hydrogen peroxide | 2 hours | 25° C | 100% | 70 : 30 |
| 0.725 gm of potassium carbonate in 30 ml of water | 0.49 gm (5.25 mmols) of 36.3% hydrogen peroxide | 2 hours | 25° C | 100% | 70 : 30 |
| 0.41 gm of sodium hydroxide in 30 ml of water | 0.49 gm (5.25 mmols) of 36.3% hydrogen peroxide | 2 hours | 25° C | 100% | 60 : 40 |
| 0.41 gm of sodium hydroxide in 30 ml of water | 0.49 gm (5.25 mmols) of 36.3% hydrogen peroxide | 2 hours | 50° C | 100% | 60 : 40 |
| 15 ml of formic acid | 0.49 gm (5.25 mmols) of 36.3% hydrogen peroxide | 2 hours | 15° C | 90% | 70 : 30 |
| 15 ml of glacial acetic acid and 1.5 ml of conc. sulfuric acid | 0.49 gm (5.25 mmols of 36.3% hydrogen peroxide | 20 minutes | 15° C | 90% | 70 : 30 |

EXAMPLE 63

Methyl-[1-(4-biphenylyl)-1-hydroxy-ethyl]-sulfoxide 21.9 gm (0.12 mol) of biphenyl-(4)-aldehyde were added in small portions to a solution of 14.8 gm (0.132 mol) of potassium tert.butylate in 110 ml of dry dimethyl sulfoxide at 20° C, and the mixture was stirred for 90 minutes at that temperature. For isolation, the mixture was diluted with 300 ml of water, and the precipitate was extracted with ethyl acetate. After washing, drying and evaporation of the extract, the residue was recrystallized from ethyl acetate and ethanol. Yield: 7.4 gm (22.2% of theory); m.p. 160-162° C.

Analysis: $C_{15}H_{16}O_2S$; mol.wt. 260.3 Calculated: C-69.20%; H-6.19%; S-12.31% Found: C-69.25%; H-6.22%; S-12.45%

NMR-spectrum (in deuterochloroform-deuteromethanol):

$CH_3$ : Singlet at 2.65 ppm $CH_2$ : between 2.95 and 3.2 ppm } second order spin
CH : between 5.1 and 5.35 ppm } spinsplitting

EXAMPLE 64

Methyl-[1-(4'-fluoro-4-biphenylyl)-1-hydroxyethyl]-sulfoxide, was prepared analogous to Example 63 from 4'-fluoro-biphenylyl-4-aldehyde and dimethyl sulfoxide in the presence of potassium-tert.butylate. Yield: 20% of theory; m.p. 167°–169° C (ethyl acetate).

Analysis: $C_{15}H_{15}FO_2S$; mol.wt. 278.36 Calculated: C-64.73%; H-5.43%; S-11.52% Found: C-64.80%; H-5.45%; S-11.35%

NMR-spectrum ($CDCl_3-CD_3OD$):
$CH_3$ : Singlet at 2.7 ppm
$CH_2$ : between 3 and 3.2 ppm } second order spin spin
CH : between 5.1 and 5.4 ppm } splitting

EXAMPLE 65

Methyl-[1-(2'-fluoro-4-biphenylyl)-1-hydroxyethyl]-sulfoxide, was prepared analogous to Example 63 from 2'-fluoro-4-biphenyl-aldehyde and dimethyl sulfoxide in the presence of potassium-tert.butylate. Yield: 11.3% of theory; m.p. 139°–141° C (ethyl acetate)

Analysis: $C_{15}H_{15}FO_2S$; mol.wt. 278.36 Calculated: C-64.73%; H-5.43%; S-11.52% Found: C-65.00%; H-5.46%; S-11.30%

NMR-spectrum ($CDCl_3-CD_3OD$):
$CH_3$ : Singelet at 2.68 ppm
$CH_2$ : between 3 and 3.25 ppm } second order spin spin
CH : between 5.1 and 5.4 ppm } splitting

EXAMPLE 66

Ethyl-[2-(2'-fluoro-4-biphenylyl)-2-oxo-ethyl]-sulfoxide 12.8 ml of 30% hydrogen peroxide were added dropwise, while stirring, to a suspension of 16.3 gm (59.5 millimols) of ethyl-[2-(2'-fluoro-4-biphenylyl)-2-oxoethyl]-sulfide in 170 ml of glacial acetic acid at 15° C. A clear solution was obtained which was stirred for 1 hour at room temperature. The reaction product was precipitated with water and recrystallized from isopropanol. Yield: 11.6 gm (67% of theory); m.p. 91-93° C.

Analysis: $C_{16}H_{15}FO_2S$; mol.wt. 290.34 Calculated: C-66.19%; H-5.20%; S-11.04% Found: C-66.10%; H-5.23%; S-11.24%

EXAMPLE 67

2-Hydroxyethyl-[2-(4-biphenylyl)-2-oxo-ethyl]-sulfoxide, was prepared analogous to Example 66 from 2-hydroxyethyl-[2-(4-biphenylyl)-2-oxo-ethyl]-sulfide by oxidation with hydrogen peroxide in glacial acetic acid. Yield: 80% of theory; m.p. 165°–167° C (from isopropanol).

Analysis: $C_{16}H_{16}O_3S$; mol.wt. 288.37 Calculated: C-66.64%; H-5.59%; S-11.12% Found: C-66.90%; H-5.66%; S-11.38%

EXAMPLE 68

2-Hydroxyethyl-[2-(2'-fluoro-4-biphenylyl)-2-oxo-ethyl]-sulfoxide, was prepared analogous to Example 66 from 2-hydroxyethyl-[2-(2'-fluoro-4-biphenylyl)-2-oxo-ethyl]-sulfide by oxidation with hydrogen peroxide in glacial acetic acid, followed by purification by column chromatography on silicagel with chloroform/methanol = 10/1. Yield: 26% of theory; m.p. 130-133° C (from isopropanol).

Analysis: $C_{16}H_{15}FO_3S$; mol.wt. 306.37 Calculated: C-62.73%; H-4.94%; S-10.47% Found: C-62.90%; H-5.04%; S-10.70%

EXAMPLE 69

2-Hydroxyethyl-[2-(4-biphenylyl)-2-hydroxy-ethyl]-sulfoxide, was prepared analogous to Example 66 from 2-hydroxy-ethyl-[2-(4-biphenylyl)-2-hydroxy-ethyl]-sulfide by oxidation with hydrogen peroxide in glacial acetic acid. Yield of diastereoisomeric mixture: 81% of theory; m.p. 153°–162° C (from n-propanol).

Analysis: $C_{16}H_{18}O_3S$; mol.wt. 290.39 Calculated: C-66.18%; H-6.25%; S-11.04 Found: C-66.40%; H-6.24%; S-10.90%

EXAMPLE 70

2-Hydroxyethyl-[2-(2'-fluoro-4-biphenylyl)-2-hydroxy-ethyl]-sulfoxide, was prepared analogous to Example 66 from 2-hydroxyethyl-[2-(2'-fluoro-4-biphenylyl)-2-hydroxy-ethyl]-sulfide by oxidation with hydrogen peroxide in glacial acetic acid. Yield of diastereoisomeric mixture: 75% of theory; m.p. 97°–106° C (from benzene).

Analysis: $C_{16}H_{17}FO_3S$; mol.wt. 308.38 Calculated: C-62.32%; H-5.56%; S-10.40% Found: C-62.45%; H-5.65%; S-10.70%

EXAMPLE 71

[2-(4-Biphenylyl)-2-oxo-ethyl-sulfinyl]-acetic acid methyl ester, was prepared analogous to Example 66 from [2-(4-biphenylyl)-2-oxo-ethylthio]-acetic acid methyl ester by oxidation with hydrogen peroxide in glacial acetic acid. Yield: 86% of theory; m.p. 160°–163° C (from chloroform).

Analysis: $C_{17}H_{16}O_4S$; mol.wt. 316.38 Calculated: C-64.54%; H-5.10%; S-9.90% Found: C-64.30%; H-5.05%; S-9.96%

EXAMPLE 72

[2-(4-Biphenylyl)-2-oxo-ethyl-sulfinyl]-acetic acid ethyl ester, was prepared analogous to Example 66 from [2-(4-biphenylyl)-2-oxo-ethylthio]-acetic acid ethyl ester by oxidation with hydrogen peroxide in glacial acetic acid. Yield: 84% of theory; m.p. 116°–118° C (isopropanol).

Analysis: $C_{18}H_{18}O_4S$; mol.wt. 330.41 Calculated: C-65.44%; H-5.49%; S-9.71% Found: C-65.50%; H-5.57%; S-9.87%

EXAMPLE 73

[2-(2'-Fluoro-4-biphenylyl)-2-oxo-ethyl-sulfinyl]-acetic acid methyl ester, was prepared analogous to Example 66 from [2-(2'-fluoro-4-biphenylyl)-2-oxo-ethylthio]-acetic acid methyl ester by oxidation with hydrogen peroxide in glacial acetic acid. Yield: 93% of theory; m.p. 143°–145° C (ethanol).

Analysis: $C_{17}H_{15}FO_4S$; mol.wt. 334.38 Calculated: C-61.06%; H-4.52%; S-9.59% Found: C-61.30%; H-4.58%; S-9.87%

EXAMPLE 74

[2-(2'-Fluoro-4-biphenylyl)-2-oxo-ethyl-sulfinyl]-acetic acid 21 gm (69 millimols) of [2-(2'-fluoro-4-biphenylyl)-2-oxo-ethylthio]-acetic acid was dissolved by means of 7.3 gm (69 millimols) of sodium carbonate in 150 ml of water at 50° C, and 11 ml of 30% hydrogen peroxide were added dropwise to the solution at that temperature. After 1 hour, the mixture was acidified with hydrochloric acid, the reaction product was suction-filtered off, washed, dried and recrystallized from ethanol. Yield: 10.8 gm (49% of theory); m.p. 154°–156° C.

Analysis: $C_{16}H_{13}FO_4S$; mol.wt. 320.35 Calculated: C-60.00%; H-4.09%; S-10.01% Found: C-60.00%; H-4.06%; S-10.05%

M.p. of the cyclohexylammonium salt of the acid: 137°–139° C (from methyl ethyl ketone).

EXAMPLE 75

[2-(4'-Fluoro-4-biphenylyl)-2-oxo-ethyl-sulfinyl]-acetic acid, was prepared analogous to Example 74 from [2-(4'-fluoro-4-biphenylyl)-2-oxo-ethylthio]-acetic acid by oxidation with hydrogen peroxide in the presence of sodium carbonate in water. Yield: 35% of theory; m.p. 144°–145° C (decomp.); m.p. of the cyclohexylammonium salt: 151°–152° C (decomp.; from isopropanol).

Analysis: $C_{22}H_{26}FNO_4S$; mol.wt. 419.52 Calculated: C-62.99%; H-6.25%; N-3.34%; S-7.64% Found: C-62.70%; H-6.20%; N-3.31%; S-7.58%

EXAMPLE 76

2-(2'-Fluoro-4-biphenylyl)-2-hydroxy-ethyl-sulfinyl]-acetic acid 5.7 gm (17.8 millimols) of [2-(2'-fluoro-4-biphenylyl)-2-oxo-ethyl-sulfinyl]-acetic acid were dissolved in 120 ml of water with 1.2 gm (22 millimols) of potassium hydroxide, and 0.35 gm (9 millimols) of sodium borohydride was added to the solution. After 1.5 hours, the mixture was acidified, the reaction product was extracted with ethyl acetate and isolated as its cyclohexylammonium salt. Yield: 4.5 gm (60% of theory); m.p. 174°–176° C (from methanol/ether = 1/3).

Analysis: $C_{22}H_{28}FNO_4S$; mol.wt. 421.54 Calculated: C-62.69%; H-6.69%; N-3.32%; S-7.60% Found: C-63.00%; H-6.65%; N-3.04%; S-7.74%

EXAMPLE 77

[2-(4-Biphenylyl)-2-oxo-ethyl-sulfinyl]-acetic acid isopropylamide

A suspension of 2.0 gm (6.1 millimols) of [2-(4-biphenylyl)-2-oxo-ethylthio]-acetic acid isopropylamide in 20 ml of glacial acetic acid was admixed with 1.3 ml of 30% hydrogen peroxide, and the mixture was stirred at room temperature for 2 hours. The reaction product was precipitated with water and recrystallized from ethyl acetate after drying. Yield: 71.4% of theory; m.p. 138°– ° C.

EXAMPLE 78

[2-(4-Biphenylyl)-2-oxo-ethylsulfinyl]-acetic acid amide, was prepared analogous to Example 77 from [2-(4-biphenylyl)-2-oxo-ethylthio]-acetic acid amide by oxidation with hydrogen peroxide in glacial acetic acid. Yield: 75% of theory; m.p. 190° C (decomp.; from n-butanol)

Analysis: $C_{16}H_{15}NO_3S$; mol.wt. 301.35 Calculated: C-63.77%; H-5.01%; N-4.64%; S-10.64% Found: C-63.50%; H-5.00%; N-4.52%; S-10.72%

EXAMPLE 79

[2-(4-biphenylyl)-2-oxo-ethylsulfinyl]-acetic acid 1-oxidothiomorpholide, was prepared analogous to Example 77 from [2-(4-biphenylyl)-2-oxo-ethylthio]-acetic acid thiomorpholide by oxidation with hydrogen peroxide in glacial acetic acid. Yield: 82% of theory; m.p. 181°–183° C (decomp.; from n-butanol).

Analysis: $C_{20}H_{21}NO_4S_2$; mol.wt. 403.49 Calculated: C-59.53%; H-5.24%; N-3.47%; S-15.89% Found: C-59.50%; H-5.29%; N-3.38%; S-15.63%

EXAMPLE 80

[2-(4-Biphenylyl)-2-oxo-ethylsulfinyl]-acetic acid anilide, was prepared analogous to Example 77 from [2-(4-biphenylyl)-2-oxo-ethylthio]-acetic acid anilide by oxidation with hydrogen peroxide in glacial acetic acid. Yield: 32% of theory; m.p. 210°–212° C (from glacial acetic acid).

Analysis: $C_{22}H_{19}NO_3S$; mol.wt. 377.44 Calculated: C-70.01%; H-5.07%; N-3.71%; S-8.49% Found: C-69.80%; H-5.01%; N-3.73%; S-8.65%

EXAMPLE 81

[2-(2'-Fluoro-4-biphenylyl)-2-oxo-ethylsulfinyl]-acetic acid isopropylamide, was prepared analogous to Example 77 from [2-(2'-fluoro-4-biphenylyl)-oxo-ethylthio]-acetic acid isopropylamide by oxidation with hydrogen peroxide in glacial acetic acid. Yield: 80% of theory; m.p. 160°–161° C (n-butanol).

Analysis: $C_{19}H_{20}FNO_3S$; mol.wt. 361.40 Calculated: C-63.14%; H-5.57%; N-3.87%; S-8.87% Found: C-62.90%; H-5.55%; N-3.87%; S-8.95%

EXAMPLE 82

[2-(2'-Fluoro-4-biphenylyl)-2-oxo-ethylsulfinyl]-acetic acid 1-oxidothiomorpholide, was prepared analogous to Example 77 from [2-(2'-fluoro-4-biphenylyl)-2-oxo-ethylthio]-acetic acid thiomorpholide by oxidation with hydrogen peroxide in glacial acetic acid. Yield: 68% of theory; m.p. 161°–162° C (n-butanol).

Analysis: $C_{20}H_{20}FNO_4S_2$; mol.wt. 421.47 Calculated: C-56.99%; H-4.78%; N-3.32%; S-15.22% Found: C-56.90%; H-4.74%; N-3.29%; S-15.32%

EXAMPLE 83

[1-(3'-Chloro-4-biphenylyl)-ethylsulfinyl]-acetic acid methyl ester 1.4 ml of 36.4% hydrogen peroxide were added dropwise to 5.0 gm (15.5 millimols) of [1-(3'-chloro-4-biphenylyl)-ethylthio]-acetic acid methyl ester in 20 ml of glacial acetic acid. After 1 hour, the mixture was evaporated in vacuo, and the residue was diluted with water and extracted with ethyl acetate. After washing, drying and evaporating the extract, 5.2 gm of an oily residue were obtained which was passed through a 500 gm-silicagel column with cyclohexane/ethyl acetate = 1/4. After evaporation of the eluate, 5.0 gm (96% of theory) of the title compound were obtained as an oil with $R_f$-values of 0.4 and 0.55 (diastereoisomeric mixture) on carrier 1 with cyclohexane/ethyl acetate = 1/4. NMR-spectrum (CDCl$_3$): CH$_2$-signals a) as double doublet at 3.46 Hz; b) as singlet at 3.34 Hz.

One diastereoisomer crystallized from isopropanol; it showed the CH$_2$-group as double doublet at 3.46 ppm (J = 14 Hz) in the NMR-spectrum (CDCl$_3$). Yield: 51.5% of theory; m.p. 85°–87° C.

Analysis: $C_{17}H_{17}ClO_3S$; mol.wt. 336.79 Calculated: C-60.63%; H:5.09%; Cl-10.53%; S-9.35% Found: C-60.70%; H-5.02%; Cl-10.52%; S-9.52%

EXAMPLE 84

(2'-Fluoro-4-biphenylmethyl)-sulfinyl-acetic acid, was prepared analogous to Example 83 from (2'- fluoro-4-biphenylylmethyl)-thioacetic acid by oxidation with hydrogen peroxide in glacial acetic acid. Yield: 88% of theory; m.p. 140°–141° C (from glacial acetic acid)

Analysis: $C_{15}H_{13}FO_3S$; mol.wt. 292.34 Calculated: C-61.63%; H-4.49%; S-10.97% Found: C-61.90%; H-4.49%; S-10.57%

EXAMPLE 85

(2'-Fluoro-4-biphenylyl)-methylsulfinyl-acetic acid methyl ester

A solution of 11.5 gm (39.3 millimols) of (2'-fluoro-4-biphenylyl)-methyl-sulfinyl-acetic acid in 60 ml of dimethyl sulfoxide, was admixed with 8.2 gm of dry potassium carbonate and 8.4 gm of methyl iodide, and the mixture was stirred at room temperature for 3 hours. Thereafter, water was added, whereupon the reaction product crystallized out and was suction-filtered off, dried and recrystallized from carbon tetrachloride and isopropanol Yield: 3.8 gm (32% of theory); m.p. 79°–80° C Analysis: $C_{16}H_{15}FO_3S$; mol.wt. 306.37 Calculated: C-62.73%; H-4.93%; S-10.47% Found: C-62.90%; H-4.92%; S-10.34%

NMR-spectrum (CDCl$_3$): CH$_2$-signals as doublets at 3.6 and 4.2 ppm.

EXAMPLE 86

[1-(2'-Fluoro-4-biphenylyl)-2-hydroxy-ethylsulfinyl]-acetic acid methyl ester, was prepared analogous to Example 83 from [1-(2'-fluoro-4-biphenylyl)-2-hydroxy-ethylthio]-acetic acid methyl ester by oxidation with hydrogen peroxide in glacial acetic acid. Yield: 85% of theory. Oily crystals (diastereoisomeric mixture) with R$_f$-values of 0.3 to 0.4 on carrier 1 with cyclohexane/ethyl acetate = 1/4. One of the two diastereoisomers had a m.p. of 123°–125° C (from benzene). In the NMR-spectrum (CDCl$_3$) the CH$_2$-group appeared as singlet at 3.4 ppm.

Analysis: $C_{17}H_{17}FO_4S$; mol.wt. 336.39 Calculated: C-60.70%; H-5.09%; S-9.53% Found: C-60.60%; H-5.11%; S-9.66%

EXAMPLE 87

[1-(4'-Fluoro-4-biphenylyl)-ethylsulfinyl]-acetic acid methyl ester, was prepared analogous to Example 83 from [1-(4'-fluoro-4-biphenylyl)-ethylthio]-acetic acid methyl ester by oxidation with hydrogen peroxide in glacial acetic acid. Yield: 70% of theory; m.p. 82°–84° C (from isopropanol). NMR-spectrum (CDCl$_3$): The CH$_2$-signals of the diastereoisomeric mixture appeared a) as double doublet at 3.5 ppm, b) as singlet at 3.33 ppm.

Analysis: $C_{17}H_{17}FO_3S$; mol.wt. 320.36 Calculated: C-63.73%; H-5.34%; S-10.01% Found: C-64.00%; H-5.34%; S-9.70%

EXAMPLE 88

[1-(4'-Chloro-4-biphenylyl)-ethylsulfinyl]-acetic acid, was prepared analogous to Example 83 from [1-(4'-chloro-4-biphenylyl)-ethylthio]-acetic acid by oxidation with hydrogen peroxide in glacial acetic acid. Yield: 96% of theory; m.p. of the diastereoisomeric mixture; 162°–163° C (decomp.; from glacial acetic acid/water = 15/35).

Analysis: $C_{16}H_{15}ClO_3S$; mol.wt. 322.82 Calculated: C-59.53%; H-4.68%; Cl-10.98%; S-9.93% Found: C-59.40%; H-4.76%; Cl-11.02%; S-9.89%

EXAMPLE 89

[1-(4'-Bromo-4-biphenylyl)-ethylsulfinyl]-acetic acid methyl ester, was prepared analogous to Example 83 from [1-(4'-bromo-4-biphenylyl)-ethylthio]-acetic acid methyl ester by oxidation with hydrogen peroxide in glacial acetic acid. Yield: 63% of theory; m.p. of the diastereoisomeric mixture: 119°–125° C (from isopropanol).

NMR-spectrum (CDCl$_3$): CH$_2$-signals a) as double doublet at
3.5 ppm; b) as singlet at 3.33 ppm Analysis: $C_{17}H_{17}BrO_3S$; mol.wt. 381.31 Calculated: C-53.55%; H-4.49%; Br-20.96%; S-8.41% Found: C-53.81%; H-4.48%; Br-21.40%; S-8.38%

EXAMPLE 90

[1-(4'-Methoxy-4-biphenylyl)-ethylsulfinyl]-acetic acid methyl ester, was prepared analogous to Example 83 from [1-(4'-methoxy-4-biphenylyl)-ethylthio]-acetic acid methyl ester by oxidation with hydrogen peroxide in glacial acetic acid. Yield: 53% of theory; m.p. 143°–145° C (from ethyl acetate/cyclohexane = 1/1).

NMR-spectrum (CDCl$_3$): CH$_2$-group as doublet at 3.45 ppm.

Analysis: $C_{18}H_{20}O_4S$; mol.wt. 332.43 Calculated: C-65.04%; H-6.06%; S-9.65% Found: C-64.90%; H-6.20%; S-9.94%

EXAMPLE 91

[1-(4'-Methyl-4-biphenylyl)-ethylsulfinyl]-acetic acid, was prepared analogous to Example 83 from [1-(4'-methyl-4-biphenylyl)-ethylthio]-acetic acid by oxidation with hydrogen peroxide in glacial acetic acid. M.p. of the isomer which is difficultly soluble in glacial acetic acid: 163°–165° C (decomp.); yield: 43.5% of theory.

EXAMPLE 92

[1-(4'-Methyl-4-biphenylyl)-ethylsulfinyl]-acetic acid methyl ester, was prepared analogous to Example 85 from [1-(4'-methyl-4-biphenylyl)-ethylsulfinyl]-acetic acid, m.p. 163°–165° C, by esterification with potassium carbonate and methyl iodide. Yield: 55% of theory; m.p. 103°–104° C (from toluene/petroleum ether).

Analysis: $C_{18}H_{20}O_3S$; mol.wt. 316.41 Calculated: C-68.32%; H-6.37%; S-10.14% Found: C-68.30%; H-6.32%; S-10.04%

NMR-spectrum (CDCl$_3$): CH$_2$-group as double doublet at 3.44 ppm (J = 15 Hz, $\delta\tau$ = 35 Hz).

EXAMPLE 93

[1-(4'-Methylmercapto-4-biphenylyl)-ethylsulfinyl]-acetic acid methyl ester, was prepared analogous to Example 83 from [1-(4'-methylmercapto-4-biphenylyl)-ethylthio]-acetic acid methyl ester by oxidation with hydrogen peroxide in glacial acetic acid, followed by purification by column chromatography on silicagel with cyclohexane/ethyl acetate = 4/1. The diastereoisomeric mixture thus obtained was an oil with an R$_f$-value from 0.3 to 0.4 on carrier 1 with cyclohexane/ethyl acetate = 4/1. Yield: 67% of theory. NMR-spectrum (CDCl$_3$): CH$_2$-signals a) as doublet at 3.5 ppm and b) as singlet at 3.35 ppm.

EXAMPLE 94

[1-(2'-Nitro-4-biphenylyl)-ethylsulfinyl]-acetic acid methyl ester, was prepared analogous to Example 83 from [1-(2'-nitro-4-biphenylyl)-ethylthio]-acetic acid methyl ester by oxidation with hydrogen peroxide in glacial acetic acid. The diastereoisomeric mixture thus obtained was an oil with the $R_f$-values 0.4 and 0.5 on carrier 1 with cyclohexane/ethyl acetate = 1/4. One of the two diastereoisomers was obtained from isopropanol in crystalline form with a yield of 44% of theory; m.p. 116°–117° C. NMR-spectrum (CDCl$_3$): CH$_2$-group as double doublet at 3.55 ppm (J = 15 Hz).

Analysis: $C_{17}H_{17}NO_5S$; mol.wt. 347.40 Calculated: C-58.78%; H-4.93%; N-4.03%; S-9.23% Found: C-58.50%; H-4.88%; N-4.15%; S-9.12%

EXAMPLE 95

[1-(2',4'-Dichloro-4-biphenylyl)-ethylsulfinyl]-acetic acid methyl ester, was prepared analogous to Example 83 from [1-(2',4'-dichloro-4-biphenylyl)-ethylthio]-acetic acid methyl ester by oxidation with hydrogen peroxide in glacial acetic acid. The diastereoisomeric mixture had a melting point of 98°–102° C; yield: 26% of theory. NMR-spectrum (CDCl$_3$): CH$_2$- signals a) as double doublet at 3.5 ppm (J = 15 Hz) and b) as singlet at 3.33 ppm.

Analysis: $C_{17}H_{16}Cl_2O_3S$; mol.wt. 371.28 Calculated: C-54.99%; H-4.34%; Cl-19.10%; S-8.64% Found: C-54.90%; H-4.51%; Cl-18.98%; S-8.44

EXAMPLE 96

[1-(2,2'-Difluoro-4-biphenylyl)-ethylsulfinyl]-acetic acid methyl ester, was prepared analogous to Example 83 from [1-(2,2'-difluoro-4-biphenylyl)-ethylthio]-acetic acid methyl ester by oxidation with hydrogen peroxide in glacial acetic acid. The diastereoisomeric mixture was an oil with the $R_f$-values 0.4 and 0.5 on carrier 1 with cyclohexane/ethyl acetate = 1/4. Yield: 87.5% of theory.
NMR-spectrum (CDCl$_3$): CH$_2$-signals as a) double doublet at 3.55 ppm (J = 15 Hz, $\delta\tau$ = 32 Hz) and as b) singlet at 3.35 ppm. One of the isomers with a CH$_2$-signal at 3.55 ppm (J = 15 Hz) was isolated as an oil by column chromatography on 50 times its amount of silicagel with cyclohexane/ethyl acetate = 1/4. Yield: 10.7% of theory. $R_f$-value = 0.4 on carrier 1 with cyclohexane/ethyl acetate = 1/4.

Analsis: $C_{17}H_{16}F_2O_3S$; mol.wt. 338.38 Calculated: C-60.34%; H-4.77%; S-9.48% Found: C-60.50%; H-5.01%; S-9.21%

EXAMPLE 97

[1-(2-Fluoro-4'-bromo-4-biphenylyl)-ethylsulfinyl]-acetic acid methyl ester, was prepared analogous to Example 83 from [1-(2-fluoro-4'-bromo-4-biphenylyl)-ethylthio]-acetic acid methyl ester by oxidation with hydrogen peroxide in glacial acetic acid. Yield of diastereoisomeric mixture: 71% of theory; oil with an $R_f$-value from 0.4 to 0.6. NMR-spectrum (CDCl$_3$): CH$_2$-signals as a) double doublet at 3.55 ppm (J = 15 Hz, $\delta\tau$ = 32 Hz) and as b) singlet at 3.35 ppm. One of the isomers was separated as an oil (CH$_2$-signal at 3.55 ppm and $R_f$-value 0.4) by column chromatography on 50-times its amount of silicagel with cyclohexane/ethyl acetate = 1/2. Yield: 11% of theory; oil with $R_f$-value 0.4 on carrier 1 with cyclohexane/ethyl acetate = 1/4.

EXAMPLE 98

[1-(2'-Cyano-4-biphenylyl)-ethylsulfinyl]-acetic acid methyl ester, was prepared analogous to Example 83 from [1-(2'-cyano-4-biphenylyl)-ethylthio]-acetic acid methyl ester by oxidation with hydrogen peroxide in glacial acetic acid, followed by purification by column chromatography on silicagel with cyclohexane/ethyl acetate = 1/4. The diastereoisomeric mixture was an oil with the $R_f$-values 0.3 and 0.4 on carrier 2 with cyclohexane/ethyl acetate = 1/4.

Analysis: $C_{18}H_{17}NO_3S$; mol.wt. 327.41 Calculated: C-66.03%; H-5.23%; N-4.28%; S-9.79% Found: C-66.00%; H-5.75%; N-3.63%; S-9.20%
NMR-spectrum (CDCl$_3$): CH$_2$-signals as a) double doublet at 3.55 ppm (J = 15 Hz) and as b) singlet at 3.38 ppm. IR-spectrum (CH$_2$Cl$_2$): CN at 2210 cm$^{-1}$, ester-CO at 1730 cm$^{-1}$.

EXAMPLE 99

[1-(4'-Chloro-4-biphenylyl)-ethylsulfinyl]-acetic acid methyl ester, was prepared analogous to Example 85 from the diastereoisomeric mixture of [1-(4'-chloro-4-biphenylyl)-ethylsulfinyl]-acetic acid and methyl iodide in dimethyl sulfoxide in the presence of potassium carbonate. The diastereoisomeric mixture was an oil with the $R_f$-values 0.4 and 0.5 on carrier 2 with cyclohexane/ethyl acetate = 1/4. Yield: 83% of theory. The two isomers (a and b) were separated by column chromatography on 100 times the amount of silicagel with cyclohexane/ethyl acetate = 1/4.

a. crystalline oil, $R_f$-value: 0.5 on carrier 2 with cyclohexane/ethyl acetate = 1/4. Yield: 15% of theory.

Analysis: $C_{17}H_{17}ClO_3S$; mol.wt. 336.79 Calculated: C-60.63%; H-5.09%; Cl-10.53%; S-9.52% Found: C-60.90%; H-5.33%; Cl-10.23%; S-9.30%
NMR-spectrum (CDCl$_3$): CH$_2$-group as singlet at 3.3 ppm.

b. Colorless needles (from isopropanol); m.p. 125°–126° C; yield: 11.5% of theory.

Analysis: $C_{17}H_{17}ClO_3S$; mol. wt. 336.79 Calculated: C-60.63%; H-5.09%; Cl-10.53%; S-9.52% Found: C-60.50%; H-5.25%; Cl-10.75%; S-9.70%
NMR-spectrum (CDCl$_3$): CH$_2$-group as double doublet at 3.45 ppm (J = 15 Hz, $\delta\tau$ = 35 Hz).
$R_f$-value: 0.4 on carrier 2 with cyclohexane/ethyl acetate = 1/4.

EXAMPLE 100

[1-(2'-Fluoro-4-biphenylyl)-ethylsulfonyl]-acetic acid 170 gm (0.556 mol) of a diastereoisomeric mixture of [1-(2'-fluoro-4-biphenylyl)-ethylsulfinyl]-acetic acid were dissolved in 1.7 liters of acetone, and a solution of 19.9 gm (0.195 mol) of concentrated sulfuric acid in 70 ml of water was added. While stirring, 67.2 gm (0.425 mol) of potassium permanganate were added in small portions, and the temperature was maintained at 20°–25° C. The mixture was stirred for 1 hour, the manganese dioxide was suction-filtered off, the filter cake was washed with acetone, and the filtrate was evaporated in vacuo. The residue was diluted with 4 liters of glacial acetic acid, and the precipitated crystalline reaction product was suction-filtered off, washed, dried and recrystallized from toluene. Yield: 158.2 gm (88.5% of theory); m.p. 144°–146° C.

Analysis: $C_{16}H_{15}FO_4S$; mol. wt. 322.37 Calculated: C-59.61%; H-4.69%; S- 9.95% Found: C-59.60%; H-4.73%; S-10.10%

EXAMPLE 101

[1-(2'-Fluoro-4-biphenylyl)-ethylsulfonyl]-acetic acid methyl ester

A solution of 20.0 gm (62 millimols) of [1-(2'-fluoro-4-biphenylyl)-ethylsulfonyl]-acetic acid in 200 ml of benzene was admixed with 3 gm (79 millimols) of methanol and then with a solution of 15.4 gm (75 millimols) of dicyclohexyl-carbodiimide in 30 ml of benzene. After 1 hour, 100 ml of water and 30 ml of 2 N acetic acid were added, and the mixture was stirred for 15 minutes. Thereafter, the dicyclohexylurea was suction-filtered off, the aqueous phase was separated from the filtrate, and the benzene phase was evaporated. The evaporation residue was recrystallized from toluene/cyclohexane = 1/3. Yield: 18.2 gm (88.8% of theory); m.p. 79-81° C. Analysis: $C_{17}H_{17}FO_4S$; mol.wt. 336.39 Calculated: C-60.70%; H-5.04%; S-9.53% Found: C-60.80%; H-5.40%; S-9.55%

IR-spectrum (methylene chloride): $SO_2$ at 1160 and 1325 $cm^{-1}$, ester CO at 1730 $cm^{-1}$.

EXAMPLE 102

[1-(2'-Fluoro-4-biphenylyl)-ethylsulfonyl]-acetic acid ethyl ester, was prepared analogous to Example 101 from [1-(2'-fluoro-4-biphenylyl)-ethylsulfonyl]-acetic acid by esterification with ethanol in the presence of dicyclohexyl-carbodiimide. Yield: 100% of theory; oil, $R_f$-value: 0.5 on carrier 1 with toluene/ethyl acetate = 9/1. Analysis: $C_{18}H_{19}FO_4S$; mol. wt. 350.42 Calculated: C-61.70%; H-5.47%; S-9.15% Found: C-61.60%; H-5.63%; S-9.05%

EXAMPLE 103

[1-(2'-Fluoro-4-biphenylyl)-ethylsulfonyl]-acetic acid n-propyl ester, was prepared analogous to Example 101 from [1-(2'-fluoro-4-biphenylyl)-ethylsulfonyl]-acetic acid by esterification with n-propanol in the presence of dicyclohexylcarbodiimide. Yield: 100% of theory; oil, $R_f$-value: 0.5 on carrier 1 with toluene/ethyl acetate = 9/1. Analysis: $C_{19}H_{21}FO_4S$; mol. wt. 364.44
Calculated: C-62.62%; H-5.81%; S- 8.80% Found: C-63.70%; H-6.17%; S-8.40%

EXAMPLE 104

[1-(2'-Fluoro-4-biphenylyl-ethylsulfonyl]-acetic acid isoamyl ester, was prepared analogous to Example 101 from [1-(2'-fluoro-4-biphenylyl)-ethylsulfonyl]-acetic acid by esterification with isoamyl alcohol in the presence of dicyclohexyl/carbodiimide. Yield: 98% of theory; oil, $R_f$-value: 0.7 on carier 1 with toluene-ethyl acetate = 9/1.

Analysis: $C_{21}H_{25}FO_4S$; mol. wt. 392.49 Calculated: C-64.27%; H-6.42%; S-8.17% Found: C-65.10A; H-6.71%; S-7.90%

EXAMPLE 105

[1-(2'-Fluoro-4-biphenylyl)-ethylsulfonyl]-acetic acid n-hexyl ester, was prepared analogous to Example 101 from [1-(2'-fluoro-4-biphenylyl)-ethylsulfonyl]-acetic acid by esterificaion with n-hexanol in the presence of dicyclohexyl/carbodiimide. Yield: 96% of theory; oil, $R_f$-value: 0.6 on carrier 1 with toluene/ethyl acetate = 9/1.

Analysis: $C_{22}H_{27}FO_4S$; mol. wt. 406.51 Calculated: C-65.00%; H-6.69%; S-7.87% Found: C-65.30%; H-6.86%; S-7.86%

EXAMPLE 106

[1-(2'-Fluoro-4-biphenylyl)-ethylsulfonyl]-acetic acid benzyl ester, was prepared analogous to Example 101 from [1(2'-fluoro-4-biphenylyl)-ethylsulfonyl]-acetic acid by esterification with benzyl alcohol in the presence of dicyclohexylcarbodiimide. Yield: 97% of theory; oil, $R_f$-value: 0.6 on carrier 1 with toluene/ethyl acetate = 9/1.

Analysis: $C_{23}H_{21}FO_4S$; mol.wt. 412.48 Calculated: C-66.97%; H-5.13 % S-7.77% Found: C-67.20%; H-5.38%; S-7.55%

EXAMPLE 107

[1-(2'-Fluoro-4-biphenylyl)-ethyl]-methylsulfone, was prepared analogous to Example 100 from [1-(2'-fluoro-4-biphenylyl)-ethyl]-methylsulfoxide by oxidation with potassium permanganate. Yield: 82% of theory; m.p. 130°-132° C (from ethanol).

Analysis: $C_{15}H_{15}FO_2S$; mol.wt. 278.35 Calculated: C-64.73%; H-5.43%; S-11.52% Found C-65.00%; H-5.59%; S-11.40%

EXAMPLE 108

[1-(2'-Fluoro-4-biphenylyl)-ethylsulfonyl]-acetic acid piperidide

A suspension of 2.1 gm (13.4 millimols) of potassium permanganate in 15 ml of water was added in small portions to a slution of 5.0 gm (13.4 millimols) of [1-(2'-fluoro-4-biphenylyl)-ethylsulfinyl]-acetic acid piperidide in 30 ml of glacial acetic acid. The temperature was maintained at 15°-20° C. The mixture was stirred for 1 hour at room temperature, then diluted with water, the manganese dioxide was reduced with sodium bisulfite, and the reaction product was extracted with ethyl acetate. After washing, drying and evaporation of the ethyl acetate extract, the residue was recrystallized from isopropanol. Yield: 65% of theory; m.p. 126° C.

Analysis: $C_{21}H_{24}FNO_3S$; mol.wt. 389.5 Calculated: C-64.76%; H-6.21%; N-3.60%; S-8.23% Found: C-64.50%; H-6.21%; N-3.74%; S-8.44%

EXAMPLE 109

[1-(2'-Chloro-4-biphenylyl)-ethylsulfonyl-acetic acid amide, was prepared analogous to Example 108 from [1-(2'-chloro-4-biphenylyl)-ethylsulfinyl]-acetic acid amide by oxidation with potassium permanganate in glacial acetic acid. Yield: 88% of theory; m.p. 173° C (decomp.) (from isopropanol).

Analysis: $C_{16}H_{16}ClNO_3S$; mol.wt. 337.84 Calculated: C-56.89%; H-4.77%; N-4.15%; Cl-10.49%; S-9.49% Found: C-57.00%; H-4.78%; N-4.18%; Cl-10.55%; S-9.62%

EXAMPLE 110

[1-(2'-Chloro-4-biphenyl)-ethylsulfonyl]-acetic acid piperidide, was prepared analogous to Example 108 from [1-(2'-chloro-4-biphenylyl)-ethylsulfinyl]-acetic acid piperidide by oxidation with potassium permanganate in glacial acetic acid. Yield: 96% of theory; oil, $R_f$-value: 0.7 on carrier 1 with toluene/ethyl acetate/methanol = 8/4/1.

Analysis: $C_{21}H_{24}ClNO_3S$; mol.wt. 405.95 Calculated: C-62.13%; H-5.96%; N-3.45%; Cl-8.73%; S-7.90% Found: C-61.90%; H-6.11%; N-3.59%; Cl-8.50%; S-7.62%

EXAMPLE 111

[1-(2'-Chloro-4-biphenylyl-ethylsulfonyl]-acetic acid morpholide, was prepared analogous to Example 108 from [1-(2'-chloro-4-biphenylyl)-ethylsulfinyl]-acetic acid morpholide by oxidation with potassium permanganate in glacial acetic acid; oil, $R_f$-value: 0.5 on carrier 1 with toluene/ethyl acetate/methanol = 8/4/1.

Analysis: $C_{20}H_{22}ClNO_4S$; mol.wt. 407.93 Calculated: C-58.89%; H-5.44%; N-3.43%; Cl-8.69%; S-7.86% Found: C-58.80%; H-5.35%; N-3.23%; Cl-8.50%; S-7.76%

EXAMPLE 112

[1(2-Fluoro- 4'-bromo-4-biphenylyl)-ethylsulfonyl]-acetic acid methyl ester, was prepared analogous to Example 108 from [1-(2-fluoro-4'-bromo-4-biphenylyl)-ethylsulfinyl]-acetic acid methyl ester by oxidation with potassium permanganate in glacial acetic acid. Yield: 95% of theory; oil, $R_f$-value: 0.6 on carrier 1 with cyclohexane/ethyl acetate = 1/1.

EXAMPLE 113

[1-(2,2'-Difluoro-4-biphenylyl)-ethylsulfonyl]-acetic acid methyl ester, was prepared analogous to Example 108 from [1-(2,2'-difluoro-4-biphenylyl)-ethylsulfinyl]-acetic acid methyl ester by oxidation with potassium permanaganate in glacial acetic acid. Yield: 97% of theory; oil, $R_f$-value; 0.6 on carrier 1 with cyclohexane/ethyl acetate = 1/1.

Analysis: $C_{17}H_{16}F_2O_4S$; mol.wt. 354.38 Calculated: C-57.62%; H-4.55% Found: C-57.80%; H-5.02%

EXAMPLE 114

[1-(3'-Chloro-4-biphenylyl)-ethylsulfonyl]-acetic acid and its sodium salt 12.0 gm (37.2 millimols) of [1-(3'-chloro-4-biphenylyl)-ethylthio]-acetic acid methyl ester were oxidized in glacial acetic acid with a suspension of 11.8 gm (74.4 millimols) of potassium permanganate in 40 ml of water. The manganese dioxide was destroyed with sodium bisulfite, the mixture was diluted with water and extracted with ethyl acetate. After evaporation of the organic extract, the methyl ester (13.0 gm) obtained as the residue was hydrolyzed with 2.5 gm of sodium hydroxide in 100 ml of methanol into the free acid by boiling for 5 minutes. 10 ml of water were added and the sodium salt was allowed to crystallize out. Yield: 8.5 gm (63% of theory); m.p. 196° C decomp.), sintering at 85° C.

Analysis: $C_{16}H_{14}ClNaO_4S$; mol.wt. 360.81 Calculated: C-53.26%; H-3.91%; Cl-9.83%; S-8.89% Found C-53.20%; H-4.06%; Cl-9.72%; S-8.74%

EXAMPLE 115

[1(4-Biphenylyl)-ethylsulfonyl]-acetic acid, was prepared analogous to Example 114 from [1(4-biphenylyl)-ethylthio]-acetic acid by oxidation with potassium permanganate. Yield: 88% of theory; m.p. 134°-135° C (from glacial acetic acid/water = 15/35).

Analysis: $C_{16}H_{16}O_4S$; mol.wt. 304.37 Calculated: C-63.14%; H-5.00%; S-10.53% Found: C-64.00%; H-5.49%; S-10.07%

EXAMPLE 116

[1-(4-Biphenylyl)-ethylsulfonyl]-acetic acid methyl ester 17.0 gm (56 millimols) of [1-(4-biphenylyl)-ethylsulfonyl]-acetic acid were dissolved in 100 ml of methanol, and 3 ml of phosphorus oxychloride were added to the solution while cooling on ice. The mixture was heated to 35° C and was then allowed to stand overnight at room temperature. The crystalline reacton product which had separated out was suction-filtered off and recrystallized from 50 ml of isopropanol. Yield: 14.8 gm (83% of theory); m.p. 79°-80° C.

Analysis: $C_{17}H_{18}O_4S$; mol.wt. 418.40 Calculated: C-64.13%; H-5.70%; S-10.07% Found: C-64.10%; H-5.96%; S-10.28%.

The compounds of the present invention, that is, those embraced by formula I above, their diastereoisomers and optically active antipodes, and their non-toxic salts, have useful pharmacodynamic properties. More particularly, they exhibit an inhibiting effect upon thrombocyte aggregation, a prolonging effect upon the bleeding time, and a lowering effect upon the cholesterol and triglyceride level in the blood in warm-blooded animals, such as cats and mice; therefore, the compounds are useful as antithrombotics, anticoagulants and anticholesteremics.

The above-indicated pharmacodynamic activities were ascertaned by the standard pharmacological test methods described below, and the tables show the results obtained from these tests for a representative number of compounds of the present invention, namely:

A = [1-(2'-Fluoro-4-biphenylyl)-ethylsulfinyl]-acetic acid methyl ester, m.p. 78°-80° C, B = [1-(2'-Fluoro-4-biphenylyl)-ethylsulfinyl]-acetic acid methyl ester, m.p. 92-94° C, C = [1-(2'-Fluoro-4-biphenylyl)-ethylsulfinyl]-acetic acid isoamyl ester, D = α,α-Dimethyl-(2'-fluoro-4-biphenylyl)-methylsulfinylacetic acid methyl ester, E = [3-(4-Biphenylyl)-butyl-(1)-sulfinyl]-acetic acid methyl ester, F = dextrorotatory [1-(2'-fluoro-4-biphenylyl)-ethylsulfinyl]-acetic acid methyl ester, G = levorotatory [1-(2'-fluoro-4-biphenylyl)-ethylsulfinyl]-acetic acid methyl ester, H = [1-(2'-Fluoro-4-biphenylyl)-ethylsulfinyl]-acetic acid methyl amide, I = [1-(2'-Fluoro-4-biphenylyl)-ethylsulfinyl]-acetic acid piperidide, J = [1-(2'-Fluoro-4-biphenylyl)-ethylsulfinyl]-acetic acid-(1-oxido-thiomorpholide), K = Methyl-[1-(4'-fluoro-4-biphenylyl)-1-hydroxyethyl]-sulfoxide, L = [2-(4-Biphenylyl)-2-oxo-ethylsulfinyl]-acetic acid methyl ester, M = [2-(2'-Fluoro-4-biphenylyl)-2-oxo-ethylsulfinyl]-acetic acid methyl ester, N = [2-(4'-Fluoro-4-biphenyl)-2-oxo-ethylsulfinyl]acetic acid, O = [1-(3'-Chloro-4-biphenylyl)-ethylsulfinyl]-acetic acid methyl ester, P = [1-(2'-Nitro-4-biphenylyl)ethylsulfinyl]-acetic acid methyl ester, Q = [1-(2,2'-Difluoro-4-biphenylyl)-ethylsulfinyl]-acetic acid methyl ester, R = [1-(2-Fluoro-4'-bromo-4-biphenylyl)-ethylsulfinyl]-acetic acid methyl ester,
S = [1-(2'-Fluoro-4-biphenylyl)-ethylsulfonyl-acetic acid methyl ester,
T = [1-(2'-Fluoro-4-biphenylyl)-ethylsulfonyl]-acetic acid isoamyl ester, and
U = [1-(2'-Fluoro-4-biphenylyl)-ethyl]-methylsulfone, compared with
V = [(4'-Chloro-4-biphenylyl)-methylsulfonyl]-acetic acid (see Example 21 of published Dutch Application No. 67.08766).

1. The inhibiting action upon thrombocyte aggregation was ascertained by the method of Born and Cross, J. Physiol. 170, 397 (1964), in the platelet-rich plasma of healthy human test subjects, by photometrically ascertaining and registering the rate of decrease of the optical density after addition of commercial collagen containing 1 mgm of collagen fibrils per ml. The angle of inclination of the density curve is a measure of the rate of aggregaton (V max.). The point on the curve which corresponded to the greatest lightpermeability was used for calculation of the optical density (o.D.).

The collagen doses were held to a minimum, but still sufficiently large to result in an irreversible aggregation. Prior to addition of collagen, each plasma sale was incubated for 10 minutes at 37° C with various amounts of the test compound. To provoke maximum aggregation, about 0.01 ml of the collagen solution was added to 1 ml of platelet-rich plasma.

The values in Table I below represent the inhibition of the aggregation rate in % (V max) and the alteration of the optical density (O.D.) in %, compared with the untreated controls, i.e. without addition of the test compound.

TABLE I

| Compound | Inhibition in % after addition of $10^{-4}$ mol/liter | |
|---|---|---|
| | V max | O.D. |
| A | 32 | 45 |
| B | 72 | 81 |
| C | 67 | 82 |
| D | 37 | 48 |
| E | 92 | 95 |
| F | 20 | 19 |
| G | 13 | 27 |
| H | 8 | 13 |
| I | 85 | 90 |
| J | 16 | 31 |
| K | 59 | 73 |
| L | 22 | 47 |
| M | 97 | 95 |
| N | — | — |
| O | 66 | 76 |
| P | 61 | 74 |
| Q | 48 | 54 |
| R | 46 | 64 |
| S | 45 | 66 |
| T | 76 | 83 |
| U | 87 | 90 |
| V | 6 | 11 |

2. The prolonging effect upon the bleeding time was ascertained by the method of Duke, J. Amer. Med. Assoc. 15, 1185 (1910). 10 mgm/kg of the test compound were given per os to non-anesthetized mice. One or three hours after administration of the test compound, about 0.5 mm was cut off from the tail of each animal, and the exuded blood was carefully soaked up with filter paper at intervals of 30 seconds. The number of drops of blood so obtained was used as a measure for the bleeding time compared to untreated animals (5 animals/test). The following table shows the results obtained.

TABLE II

| Compound | Prolongation of bleeding time in % after | |
|---|---|---|
| | 1 hour | 3 hours |
| A | 136 | 66 |
| B | 142 | 56 |
| C | 112 | 49 |
| D | 71 | — |
| E | 188 | 85 |
| F | 117 | — |
| G | 129 | — |
| H | 64 | — |
| I | 122 | — |
| J | 149 | — |
| K | 68 | 30 |
| L | 120 | 78 |
| M | 90 | 39 |
| N | 98 | 37 |
| O | 12 | — |
| P | 15 | — |
| Q | 73 | — |
| R | 50 | — |
| S | 83 | 27 |
| T | 51 | — |
| U | 56 | — |
| V | 3 | — |

3. Acute toxicity:

The acute toxicity of the test compounds was determined in white mice (observation time: 14 days) after oral administration of a single dose.

TABLE III

| Compound | acute toxicity |
|---|---|
| A | > 2000 mgm/kg (1 out of 10 animals died) |
| B | > 500 mgm/kg (2 out of 5 animals died) |
| C | > 250 mgm/kg (1 out of 5 animals died) |
| D | > 250 mgm/kg (2 out of 5 animals died) |
| E | > 250 mgm/kg (0 out of 5 animals died) |
| F | — |
| G | — |
| H | > 250 mgm/kg p.o. (0 out of 5 animals died) |
| I | > 250 mgm/kg p.o. (0 out of 5 animals died) |
| J | > 250 mgm/kg p.o. (0 out of 5 animals died) |
| K | — |
| L | — |
| M | — |
| N | — |
| O | > 250 mgm/kg p.o. (0 out of 5 animals died) |
| P | > 250 mgm/kg p.o. (0 out of 5 animals died) |
| Q | > 250 mgm/kg p.o. (0 out of 5 animals died) |
| R | — |
| S | > 250 mgm/kg p.o. (0 out of 5 animals died) |
| T | > 250 mgm/kg p.o. (0 out of 5 animals died) |
| U | > 250 mgm/kg p.o. (0 out of 5 animals died) |
| V | > 250 mgm/kg p.o. (3 out of 10 animals died) |

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antithrombotic, anticoagulant or anticholesteremic dosage unit of the compounds according to the present invention is from 0.083 to 1.67 mgm/kg body weight, preferably 0.16 to 0.84 mgm/kg body weight. The daily dose rate is from 1.66 to 3.34 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 117

Tablets

The tablet composition is compounded from the following ingredients:

| | | |
|---|---|---|
| [1-(2'-Fluoro-4-biphenylyl)-ethylsulfinyl]-acetic acid methyl ester | 30.0 | parts |
| Lactose | 38.0 | '' |
| Potato starch | 26.0 | '' |
| Polyvinylpyrrolidone | 5.0 | '' |
| Magnesium stearate | 1.0 | '' |
| Total | 100.0 | parts |

Preparation:

The biphenylyl derivative is intimately admixed with the lactose and the potato starch, the mixture is uniformly moistened with an ethanolic 20% solution of the polyvinylpyrrolidone, the moist mass is forced through a 1.5 mm-mesh screen, and the resulting granulate is dried at 45° C and again passed through a 1.0 mm-mesh screen. The dry granulate thus obtained is admixed with the magnesium stearate, and the composition is compressed into 100 mgm-tablets in a conventional tablet making machine. Each tablet contains 30 mgm of the biphenylyl derivative and is an oral dosage unit composition with effective antithrombotic, anticoagulant and anticholesteremic action.

EXAMPLE 118

Coated Pills

The pill core composition is compounded from the following ingredients:

| | | |
|---|---|---|
| [1-(2'-Fluoro-4-biphenylyl)-ethylsulfinyl]-acetic acid methyl ester | 15.0 | parts |
| Lactose | 14.0 | '' |
| Corn starch | 8.0 | '' |
| Polyvinylpyrrolidone | 2.5 | '' |
| Magnesium stearate | 0.5 | '' |
| Total | 40.0 | parts |

Preparation:

The ingredients are composed in a manner analogous to that described in the preceding example, and the composition is compressed into 40 mgm-pill cores, which are subsequently coated with a thin shell consisting essentially of a mixture of talcum and sugar and finally polished with beeswax. Each coated pill contains 15 mgm of the biphenylyl derivative and is an oral dosage unit composition with effective antithrombotic, anticoagulant and anticholesteremic action.

EXAMPLE 119

Hypodermic Solution

The solution is compounded from the following ingredients:

| | | |
|---|---|---|
| [1-(2'-Fluoro-4-biphenylyl)-ethylsulfinyl]-acetic acid methyl ester | 10.0 | parts |
| Polyethyleneglycol 600 | 100.0 | '' |
| Distilled water q.s.ad | 2000.0 | '' by vol. |

Preparation:

The polyethyleneglycol and the biphenylyl derivative are dissolved in a sufficient amount of distilled water which had previously been boiled and cooled in an atmosphere of nitrogen; the dissolution is also carried out in an atmosphere of nitrogen. The resulting solution is diluted to the indicated volume with additional pretreated distilled water, and the resulting solution is filled, again in an atmosphere of nitrogen, into brown 2 cc-ampules which are then sealed and sterilized for 20 minutes at 120° C. The entire operation must be performed in diffused light. Each ampule contains 10 mgm of the biphenylyl derivative and the contents thereof are an injectable dosage unit composition with effective antithrombotic, anticoagulant and anticholesteric action.

EXAMPLE 120

Drop Solution

The solution is compounded from the following ingredients:

| | | |
|---|---|---|
| [1-(2'-Fluoro-4-biphenylyl)-ethylsulfinyl]-acetic acid methyl ester | 10.0 | parts |
| Cane sugar | 350.0 | '' |
| Essence of cocoa | 50.0 | '' |
| Sorbic acid | 1.0 | '' |
| Ethyl alcohol | 200.0 | by vol. |
| Polyethyleneglycol 600 | 100.0 | '' |
| Distilled water q.s.ad | 1000.0 | '' |

Preparation:

The sorbic acid is dissolved in the ethanol, the solution is diluted with an equal volume of distilled water, and the biphenylyl derivative is dissolved in the aqueous mixture (solution 1). The cane sugar is dissolved in the remaining amount of distilled water (solution 2). Solution 2, the polyethyleneglycol and the essence of cocoa are stirred into solution 1, and the composition is filtered. The entire operation must be performed in an atmosphere of nitrogen and in diffused light. 1 ml of the filtrate (about 20 drops) contains 10 mgm of the biphenylyl derivative and is an oral dosage unit composition with effective antithrombotic, anticoagulant and anticholesteremic action.

Analogous results are obtained when any one of the other biphenylyl derivatives of the present invention is substituted for the particular biphenylyl derivative in Examples 117 through 120. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula
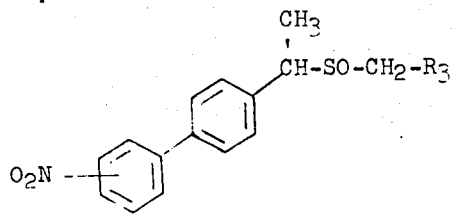
wherein $R_3$ is (alkoxy of 1 to 6 carbon atoms)-carbonyl; a diastereoisomer thereof; or an optically active antipode thereof.
2. A compound of claim 1, which is methyl [1-(2'-nitro-4-biphenylyl)-ethylsulfinyl]-acetate, a diastereoisomer thereof or an optically active antipode thereof.
* * * * *

UNITED STATES PATENT OFFICE
CERTIFICATE OF CORRECTION

Patent No. 3,993,683      Dated November 23, 1976

Inventor(s) JOSEF NICKL, ERICH MÜLLER, BERTHOLD NARR, WALTER HAARMAN, WOLFGANG SCHRÖTER, RUDOLF KADATZ It is certified that error appears in the above-identified patent and that said Letters Patent are hereby corrected as shown below:

| | |
|---|---|
| Col. 4, line 51 | before "Silicagel" insert -- = -- |
| Col. 4, line 51 | delete "Siliagel" |
| Col. 4, line 51 | "prepared" should read -- preprepared -- |
| Col. 6, line 46 | before "[" insert -- 1. -- |
| Col. 8, line 52 | "a" should read -- at -- |
| Col. 16, line 50 | "actic" should read -- acetic -- |
| Col. 24, line 44 | "NC-3.75%" should read -- N-3.75% -- |
| Col. 24, line 44 | "NC-3.32%" should read -- N-3.32% -- |
| Col. 29, line 51 | before "°C" insert -- 139 -- |
| Col. 38, line 10 | "reacton" should read -- reaction -- |

Signed and Sealed this

Twelfth Day of April 1977

[SEAL]

Attest:

RUTH C. MASON
Attesting Officer

C. MARSHALL DANN
Commissioner of Patents and Trademarks